United States Patent
Park et al.

(10) Patent No.: US 8,424,345 B2
(45) Date of Patent: Apr. 23, 2013

(54) WASHING MACHINE, CONDUCTIVITY SENSOR IN WASHING MACHINE, AND CONTROLLING METHOD OF THE SAME

(75) Inventors: Yong Suck Park, Changwon (KR); Young Han Song, Changwon (KR)

(73) Assignee: LG Electronics Inc., Seoul (KR)

( * ) Notice: Subject to any disclaimer, the term of this patent is extended or adjusted under 35 U.S.C. 154(b) by 1752 days.

(21) Appl. No.: 10/499,342

(22) PCT Filed: Nov. 27, 2003

(86) PCT No.: PCT/KR03/02583
§ 371 (c)(1), (2), (4) Date: Jun. 17, 2004

(87) PCT Pub. No.: WO2004/048676
PCT Pub. Date: Jun. 10, 2004

(65) Prior Publication Data
US 2005/0081572 A1 Apr. 21, 2005

(30) Foreign Application Priority Data

| Date | | |
|---|---|---|
| Nov. 28, 2002 | (KR) | 10-2002-0075008 |
| Nov. 29, 2002 | (KR) | 10-2002-0075356 |
| Jan. 28, 2003 | (KR) | 10-2003-0005592 |
| Mar. 31, 2003 | (KR) | 10-2003-0020211 |
| Apr. 2, 2003 | (KR) | 10-2003-0020832 |
| Apr. 2, 2003 | (KR) | 10-2003-0020833 |
| Apr. 2, 2003 | (KR) | 10-2003-0020834 |
| Apr. 4, 2003 | (KR) | 10-2003-0021446 |

(51) Int. Cl.
*B08B 3/12* (2006.01)
*D06F 37/00* (2006.01)

(52) U.S. Cl.
USPC .................................. 68/3 R; 8/158

(58) Field of Classification Search .................. None
See application file for complete search history.

(56) References Cited

U.S. PATENT DOCUMENTS

| | | | |
|---|---|---|---|
| 3,223,108 A | | 12/1965 | Martz, Jr. |
| 4,196,384 A | * | 4/1980 | Willenbrock et al. ........ 324/446 |
| 4,257,708 A | | 3/1981 | Fukuda |
| 4,835,991 A | * | 6/1989 | Knoop et al. ............... 68/12.19 |
| 5,315,847 A | * | 5/1994 | Takeda et al. .............. 68/12.02 |
| 5,335,524 A | * | 8/1994 | Sakane ....................... 68/12.04 |
| 5,774,996 A | * | 7/1998 | Ogawa et al. .............. 33/366.12 |

FOREIGN PATENT DOCUMENTS

| | | |
|---|---|---|
| DE | 8234663 U1 | 6/1983 |
| DE | 19541719 A1 | 5/1997 |
| DE | 19858386 A1 | 6/2000 |
| EP | 0117471 A2 | 9/1984 |
| EP | 0633342 A | 1/1995 |
| JP | 55068384 | 5/1980 |
| JP | 61-201684 | 9/1986 |
| JP | 4 288194 | 10/1992 |
| JP | 05015690 | 1/1993 |

(Continued)

*Primary Examiner* — Michael Barr
*Assistant Examiner* — Jason Ko
(74) *Attorney, Agent, or Firm* — McKenna Long & Aldridge LLP

(57) ABSTRACT

There are provided a conductivity sensor of a washing water, an installation construction of the conductivity sensor, and a method for controlling the washing machine, which are capable of controlling the washing machine by calculating a hardness of a washing water from a measured conductivity of the washing water.

12 Claims, 26 Drawing Sheets

FOREIGN PATENT DOCUMENTS

| | | |
|---|---|---|
| JP | 06-218183 | 8/1994 |
| JP | 06233892 | 8/1994 |
| JP | 07-039677 | 2/1995 |
| JP | 10-153481 | 6/1998 |
| JP | 2001-017775 | 1/2001 |
| JP | 2001-293284 | 10/2001 |
| JP | 2002-050428 | 2/2002 |
| JP | 2002-305065 | 10/2002 |
| JP | 2003-163051 | 6/2003 |
| JP | 2004-082585 | 3/2004 |
| JP | 2004-083613 | 10/2004 |

* cited by examiner

WASHING MACHINE, CONDUCTIVITY SENSOR IN WASHING MACHINE, AND CONTROLLING METHOD OF THE SAME

This application claims priority from Korean Patent Application No. 2002-75008 filed Nov. 28, 2002, Korean Patent Application No. 2002-75356 filed Nov. 29, 2002, Korean Patent Application No. 2003-5592 filed Jan. 28, 2003, Korean Patent Application No. 2003-20211 filed Mar. 31, 2003, Korean Patent Application No. 2003-20833 filed Apr. 2, 2003, Korean Patent Application No. 2003-20832 filed Apr. 2, 2003, Korean Patent Application No. 2003-20834 filed Apr. 2, 2003 and Korean Patent Application No. 2003-21446 filed Apr. 4, 2003 which are hereby incorporated by reference as if fully set forth herein.

TECHNICAL FIELD

The present invention relates to a washing machine capable of measuring a hardness of a washing water, a conductivity sensor thereof and a controlling method thereof, and more particularly, to a washing machine, a conductivity sensor thereof, and a controlling method of the washing machine having the conductivity sensor, which are capable of improving a washing efficiency by applying a different controlling method according to a hardness of a washing water.

BACKGROUND ART

In general, various sensors are installed in a washing machine to sense several washing conditions necessary for a washing operation. The washing machine is appropriately driven according to the sensed washing conditions in order to obtain the maximum washing effect. As sensors of a conventional washing machine, a sensor for sensing an amount of washing water received in a washing tub and a sensor for measuring a water temperature in order to boil the laundry have been proposed and used.

Meanwhile, one of factors that determine properties of the washing water is a water hardness. The water hardness is a term that represents a degree of a water strength. Materials determining the hardness are calcium, magnesium, iron, strontium, and the like. As well known, in case the water harness is high, a detergent is not dissolved well due to magnesium ions or calcium ions contained in the water, so that a cleaning capacity of the detergent is degraded. Accordingly, the water having a high hardness is not suitable for domestic water or industrial water.

However, the related art has not proposed a method for adjusting an amount of detergent and water in the washing machine according to the hardness of the washing water. Although different areas have different water hardness, the equal method of inputting detergent and water is applied at every area, which is one of factors that degrade the washing efficiency. Specifically, in an area where underground water is used as the washing water, an equal amount of detergent and water is used while the hardness of the washing water is ignored. This is an important factor that degrades the washing efficiency.

DISCLOSURE OF THE INVENTION

Accordingly, the present invention is directed to a washing machine that substantially obviates the problems caused by limitations and disadvantage of the conventional one.

One object of the present invention is to provide a washing machine and a washing method, in which the optimum washing efficiency is obtained by properly changing a washing method according to a hardness of a washing water.

Another object of the present invention is to provide a washing machine and a washing method, in which the reliability is improved by using a measured conductivity of a washing water as various indexes of an operation of the washing machine.

Further another object of the present invention is to provide a washing machine and a washing method, in which a conductivity sensor for sensing a conductivity of a washing water is installed stably, thereby preventing leakage of the washing water, stably measuring a hardness of the washing water, and stably operating the washing machine.

According to one aspect of the present invention, a washing machine includes: a pair of electrodes formed inside an outer tub containing a washing water, in which the pair of electrodes contact with the washing water to measure a conductivity of the washing water; and a controller for controlling the washing machine according to the measured conductivity of the washing water.

According to another aspect of the present invention, a conductivity sensor of a washing machine includes: a pair of electrodes formed at one side of an outer tub, in which the pair of electrodes contact with a washing water to measure a conductivity of the washing water; a protection member for protecting the electrodes that pass through the protection member; a housing in which one side of the protection member is sealed; and a sealing member formed in at least a contact surface between the protection member and the electrodes.

According to further another aspect of the present invention, a conductivity sensor of a washing machine includes: a pair of electrodes formed at one side of an outer tub, in which the pair of electrodes contact with a washing water to measure a conductivity of the washing water; a connector extended from the electrodes to act as a terminal for outputting an electrical signal; and a receptacle fitted into the connector to transmit the electrical signal.

According to further another aspect of the present invention, a method for controlling a washing machine includes the steps of: measuring a conductivity of a washing water; determining a hardness of the washing water by using the measured conductivity; and performing a washing operation according to the determined hardness.

According to the present invention, the reliability in the operation of the washing machine can be improved. Specifically, the washing efficiency can be improved by adjusting an amount of detergent and washing water according to the hardness of the washing water, which is sensed by the conductivity sensor.

Further, according to the present invention, the conductivity sensor is stably operated, thereby preventing an erroneous operation of the conductivity sensor, which may be caused by leakage of water and foreign substance.

BRIEF DESCRIPTION OF THE DRAWINGS

The above objects, other features and advantages of the present invention will become more apparent by describing the preferred embodiments thereof with reference to the accompanying drawings, in which.

BEST MODE FOR CARRYING OUT THE INVENTION

Hereinafter, preferred embodiments of the present invention will be described in detail with reference to the attached drawings. The present invention is not limited to the embodiments and it will be apparent to those skilled in the art that the present invention can be easily applied to other embodiments within the spirit and scope of the present invention.

First Embodiment

A first embodiment of the present invention will be described in detail with reference to FIGS. 1 to 3.

Figure 1:
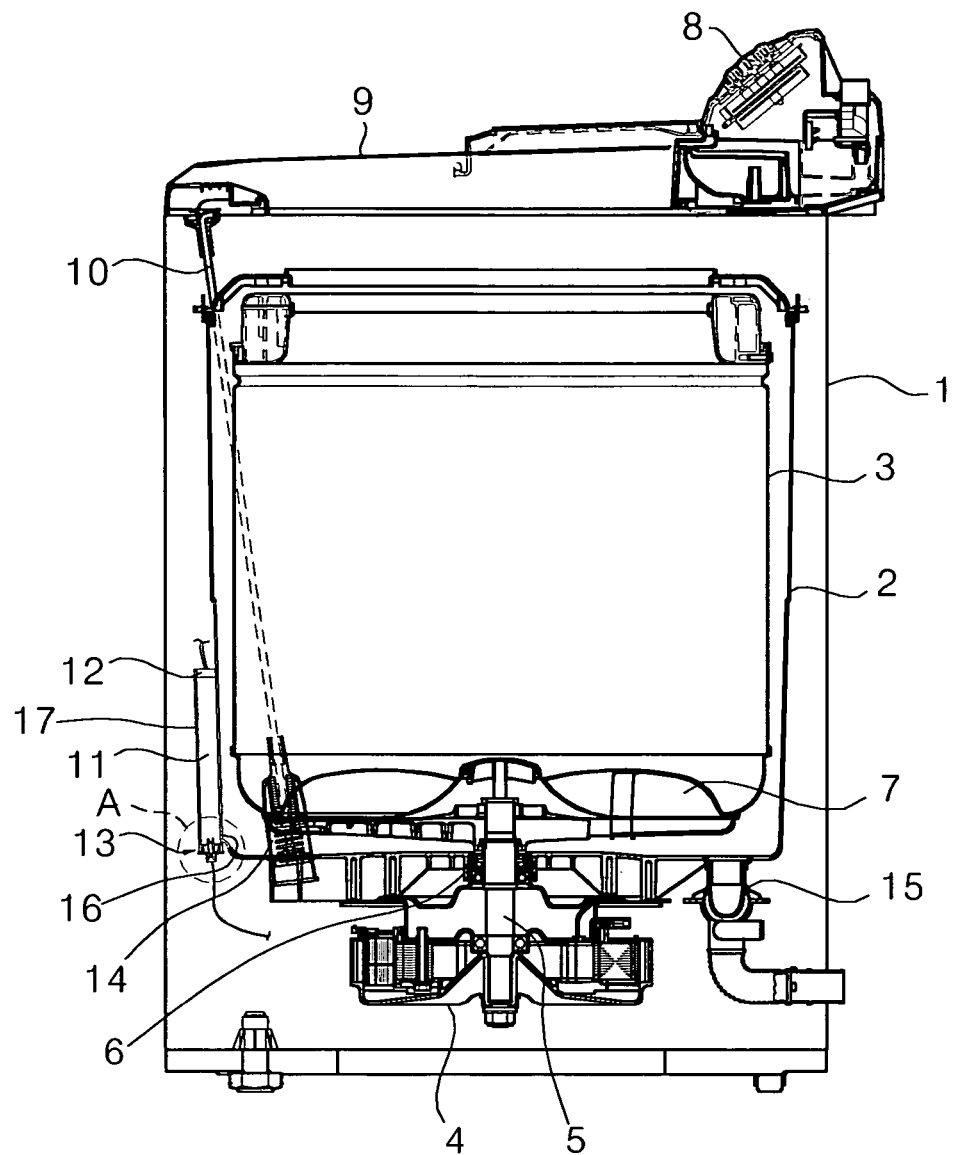
FIG. 1 is a sectional view of a washing machine according to a first embodiment of the present invention.

FIG. 1 is a sectional view of a washing machine according to a first embodiment of the present invention.

Referring to FIG. 1, the washing machine according to the present invention includes: a cabinet 1 forming an outer shell; an outer tub 2 fixedly suspended inside the cabinet 1 by a plurality of suspension members 10, for containing a washing water; a damper 14 formed on a lower portion of the suspension member 10 to attenuate a vibration of the outer tub 2; an inner tub 3 rotatably installed inside the outer tub 2 to receive a laundry and a washing water supplied through a supply valve; a pulsator 7 rotatably installed in a lower portion of the inner tub 3 to agitate a water current of the washing water; a drive motor 4 driven by an external power; a drive shaft 5 disposed at a central portion of the drive motor 4; a clutch 6 installed in a lower portion of the outer tub 2 to selectively rotate the inner tub 3 or the pulsator 7; a manipulation/control unit 8 for controlling a washing cycle and operation of the washing machine; a drain port 15 installed in a lower portion of the outer tub 2 to discharge the washing water from the outer tub 2; a door 9 mounted on an upper portion of the cabinet 1 to prevent the laundry from being departed from the cabinet 1 and to prevent an accident; an inlet/outlet port 16 provided at an opened lower portion of the outer tub 2 and through which the washing water is introduced and discharged; a pneumatic chamber 11 formed on an outer side of the inlet/outlet port 16; a chamber housing 17 having a wall structure for hermetically sealing the pneumatic chamber 11; a water level sensor 12 formed on an upper portion of the pneumatic chamber 11; and a conductivity sensor 13 sealed in a lower portion of the pneumatic chamber 11.

Specifically, a microprocessor and a digital storage media are installed inside the manipulation/control unit 8 to control an overall operation of the washing machine.

Herein, an operation of the washing machine will be described below.

A laundry is put in the tub through the door 9 and the washing machine begins to operate under a control of the manipulation/control unit 8. A power applied through the motor 4, the drive shaft 5 and the clutch 6 in sequence is supplied to the pulsator 7, such that the pulsator 7 rotates. The pulsator 7 rotates the washing water and the laundry and causes a friction therebetween. In this manner, a washing operation is performed. After the washing operation is completed, the wastewater is discharged through the drain port 15.

In addition, an overall cycle of the washing machine is controlled through the manipulation/control unit 8. A predetermined program stored in the storage media controls the motor 4, a supply/drain value and the clutch 6, such that an overall operation of the washing machine is controlled properly.

Further, the damper 14 is connected to the cabinet 1 through the suspension member 10. The damper 14 attenuates a vibration of the outer tub 2 to thereby reduce a vibration and movement of the body of the washing machine.

Herein, a sensing means for sensing a quantity and property of the washing water will be described in detail. If the washing water is introduced, the washing water is introduced into the pneumatic chamber 11 through the inlet/outlet port 16. The conductivity sensor 13 measures a conductivity of the washing water introduced into the pneumatic chamber 11, and a hardness of the washing water is sensed using the measured conductivity with reference to a predetermined table. The table can be stored in the digital storage media and can be read/controlled by the microprocessor. Here, the digital storage media and the microprocessor are installed inside the manipulation/control unit 8.

In addition, if the washing water continues to be introduced, a water level inside the pneumatic chamber 11 also rises. At this time, since the inside of the pneumatic chamber 11 is in a hermetically sealed state, the washing water is not discharged. Therefore, as the washing water is introduced into the outer tub 2, the internal pressure of the pneumatic chamber 11 increases. The water level of the washing water introduced inside the outer tub 2 can be measured using a pneumatic of the pneumatic chamber 11.

Specifically, a hydraulic pressure in a lower portion of the pneumatic chamber 11 is a sum of an air pressure in the inside of the pneumatic chamber 11 and a hydraulic pressure caused due to a water level of the pneumatic chamber 11. The hydraulic pressure in the lower portion of the pneumatic chamber 11 is identical to a total hydraulic pressure in the inside of the outer tub 2. Therefore, the water level of the outer tub 2 can be sensed using the air pressure in the inside of the pneumatic chamber 11. In other words, as the water level of the outer tub 2 rises higher, the air pressure in the inside of the pneumatic chamber 11 increases higher. The water level of the outer tub 2 can be sensed by inversely using a linear relationship of the increasing hydraulic pressure.

Figure 2:
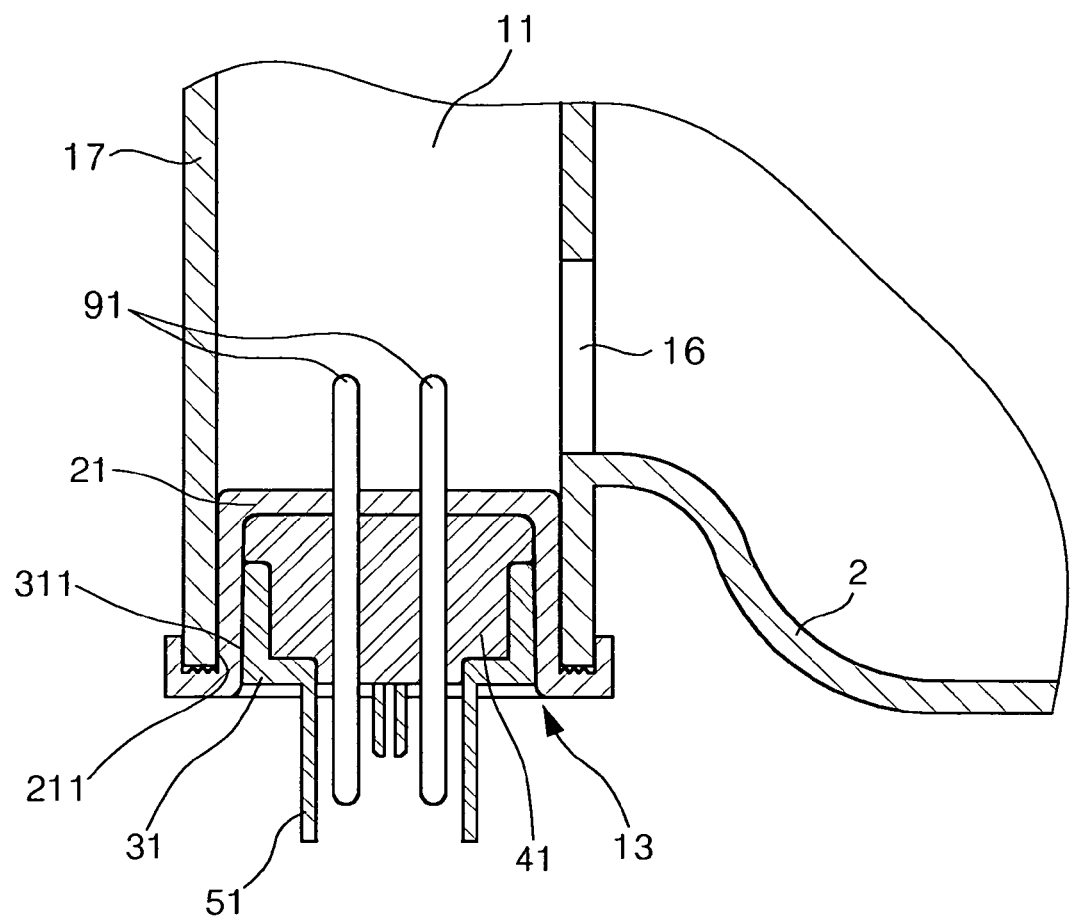
FIG. 2 is an enlarged sectional view of the portion "A" shown in FIG. 1.
Figure 3:
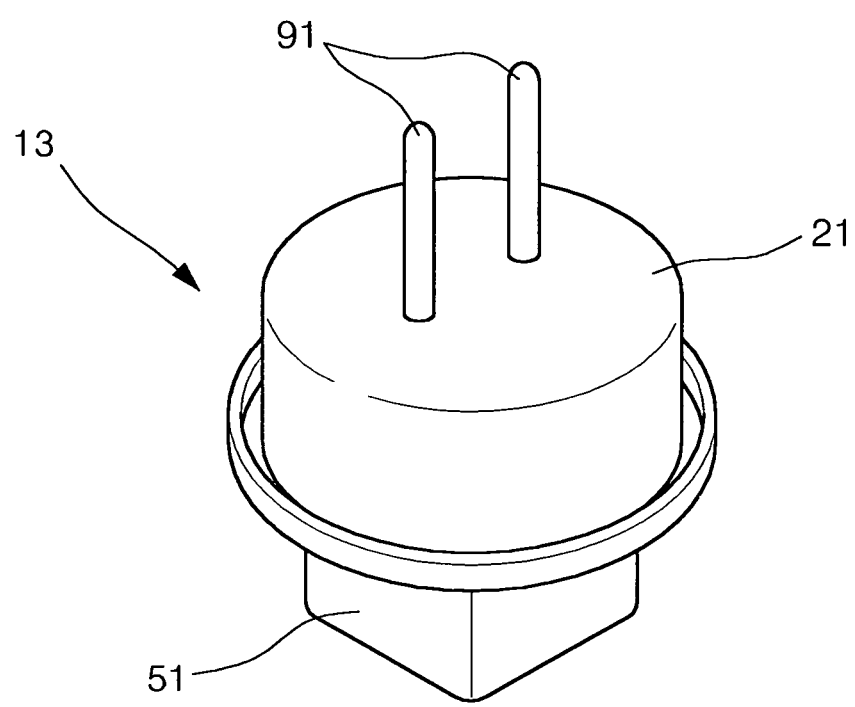
FIG. 3 is a perspective view of a conductivity sensor according to a first embodiment of the present invention.

FIG. 2 is an enlarged sectional view of the portion "A" shown in FIG. 1, and FIG. 3 is a perspective view of a conductivity sensor.

Referring to FIGS. 2 and 3, the conductivity sensor 13 includes: a pair of electrodes 91 formed of a conductive material in a bar shape; an upper protection member 21 for supporting and protecting an upper portion of the electrodes 91; a lower protection member 21 for supporting and protecting a lower portion of the electrodes 91; a sealing member 41 filled inside the protection members 21 and 31; an upper fixing portion 211 in which the upper protection member 21 and the chamber housing 17 are coupled to each other; a lower fixing portion 311 in which the upper protection member 21 and the lower protection member 31 are coupled to each other; and a connector 51 extended downward from the lower protection member 31.

Specifically, the conductivity sensor 13 according to the present invention is insertedly installed in an opening of a lower portion of the chamber housing 17 and coupled with the chamber housing 17 at the upper fixing portion 211. The upper fixing portion 211 can be fixed in any manner, for example, a fusion, an adhesion, a latching structure having a sealing member intervened therein. Of course, the lower fixing portion 311 can also be fixed by a fusion, an adhesion, a latching structure having a sealing member intervened therein.

In more detail, the pair of the electrodes 91 are formed, and a protruded upper end portion of each electrode 91 protruded inside the pneumatic chamber 11 keeps in contact with the washing water. Accordingly, the electrodes 91 must be made of material, such as stainless or copper, which has a high conductivity and a high corrosion resistance. Among the electrodes 91, one flows an electric current into the washing water and the other senses an amount of electric current flowing into the washing water. In this manner, the quantity of ions contained in the washing water can be sensed according to the amount of the electric current and the hardness of the washing water can be measured according to the sensed quantity of ions. For example, in case a large quantity of ions exists so that the hardness is high, there is a large amount of electric current and a resistance becomes small. Meanwhile, in case there is a small quantity of ions so that the hardness is low, there is a small amount of electric current and a resistance becomes large.

In addition, the sealing member 41 can be made of rubber or epoxy material. The sealing member 41 is interposed among the protection members 21 and 31 and the electrodes 91 and prevents any leakage of the washing water contained in the pneumatic chamber 11. The sealing member 41 can be formed by filling an inner space of the upper protection member 21 with a liquid material and then compressing it by a thrust of the lower protection member 31.

A receptacle in which a predetermined terminal is formed is inserted into the connector 51 to thereby transfer the amount of electric current, sensed by the electrodes 91, to the manipulation/control unit 8 in a stable state.

In this embodiment, the conductivity of the washing water introduced through the inlet/outlet port 16 is measured through the electrodes 91 and the hardness of the washing water is determined according to the measured conductivity. The washing machine can be controlled appropriately by changing the control method of the washing machine according to the determined hardness of the washing water. For example, in case the hardness of the washing water is high, an amount of detergent necessary for washing the laundry is increased. Meanwhile, in case the hardness of the washing water is low, an amount of detergent necessary for washing the laundry is reduced.

In addition, the sealing member 41, the upper fixing portion 211 and the lower fixing portion 311 can prevent leakage of air or water, which is received in the pneumatic chamber 11.

Second Embodiment

A second embodiment of the present invention will be described in detail with reference to FIGS. 4 to 6.

Figure 4:
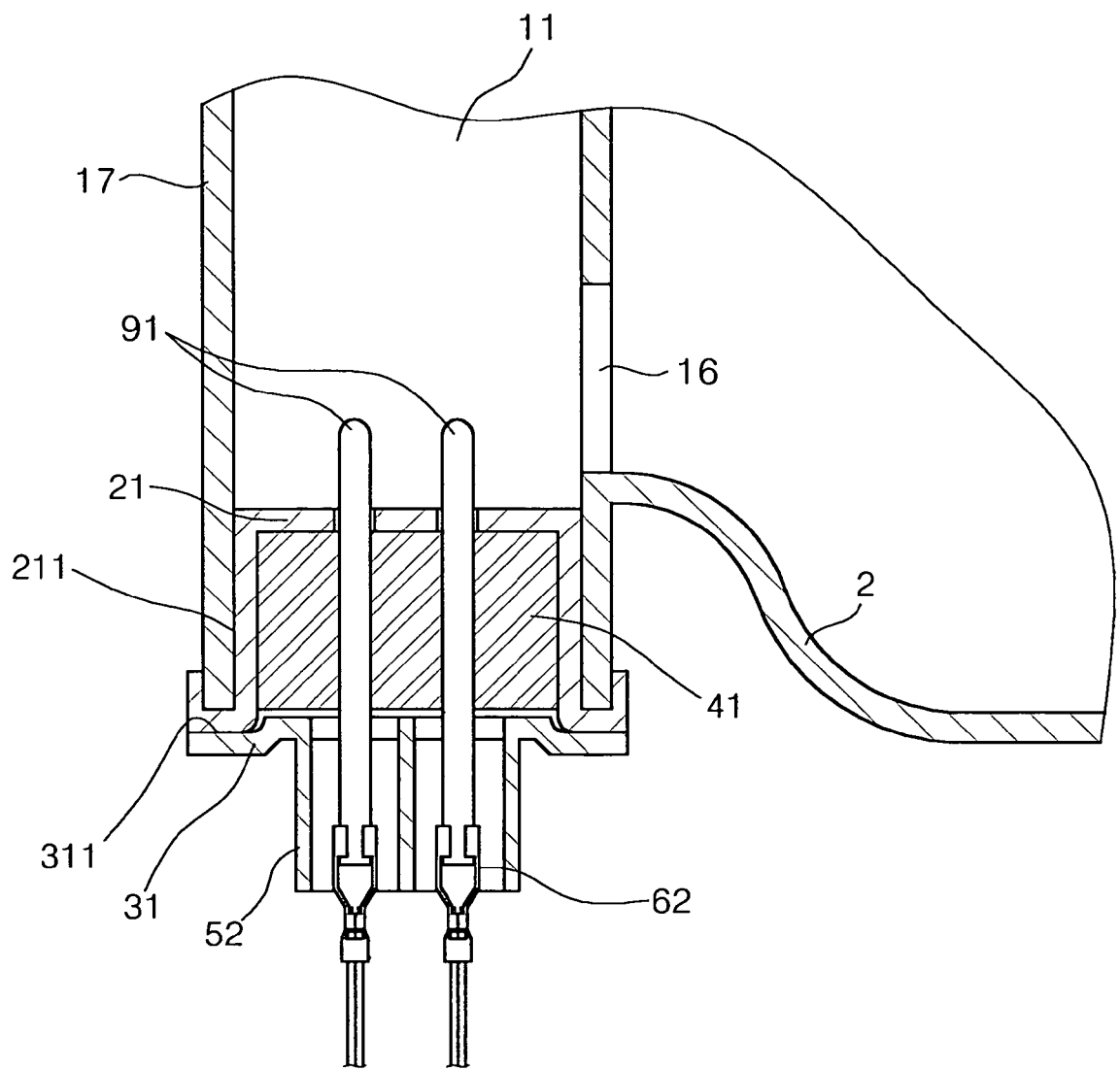
FIG. 4 is a sectional view of a conductivity sensor and an installation construction thereof according to a second embodiment of the present invention.

FIG. 4 is a sectional view of a conductivity sensor and an installation construction thereof according to the second embodiment of the present invention.

Referring to FIG. 4, the conductivity sensor according to the second embodiment of the present invention includes a pair of electrodes 91, an upper protection member 21, a lower protection member 31, a sealing member 41, an upper fixing portion 211 and a lower fixing portion 311, which are identical to those of the first embodiment described above. A difference is that the conductivity sensor further includes a connector 52 extended downward from the lower protection member 31, and a receptacle 62 formed in an inside of the connector 52 and fixed to a lower portion of each electrode in order to apply an electric current, in which the lower portion of each electrode is formed in a circular bar shape.

Figure 5:
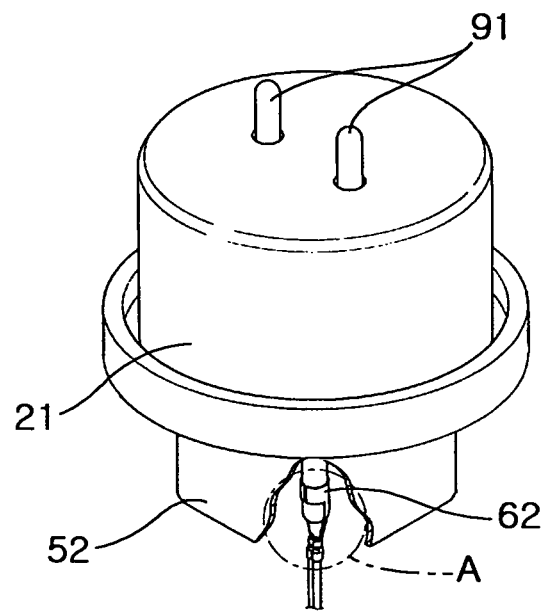
FIG. 5 is a perspective view of the conductivity sensor according to the second embodiment of the present invention.
Figure 6:
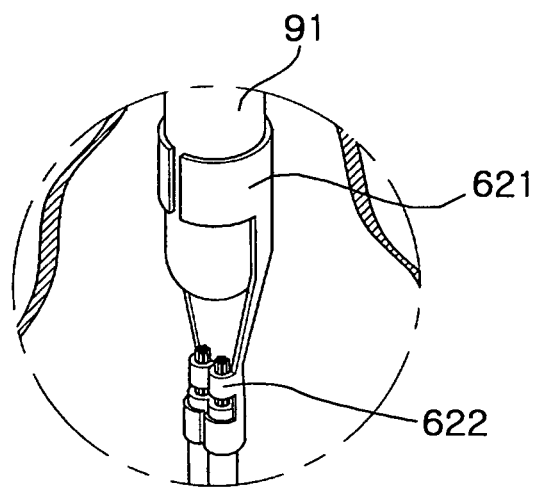
FIG. 6 is an enlarged view of a receptacle according to a second embodiment of the present invention.

FIG. 5 is a perspective view of the conductivity sensor according to the second embodiment of the present invention, and FIG. 6 is an enlarged view of the portion "A" shown in FIG. 5.

Referring to FIGS. 5 and 6, the electrode 91 has the lower portion formed in a circular bar shape, and the receptacle 62 includes a receptacle fixing part 621 and a wire fixing part 622. The receptacle fixing part 621 is rolled around an outer periphery of the electrode 91, and the wire fixing part 622 is formed at a lower end portion of the receptacle 62 as one body with the receptacle fixing part 621. According to the construction described above, the voltage sensed by the electrodes 91 can be accurately transferred to the manipulation/control unit 8, and the structure for coupling the electrodes 91 and the receptacle 62 can be fixed regardless of the vibration of the washing machine.

Meanwhile, the receptacle fixing part 621 can be provided by rolling a flat-shaped conductor around the outer periphery of the electrode 91 or can be fixed by forceably inserting the electrode 91 into the receptacle fixing part 621.

Third Embodiment

Figure 7:
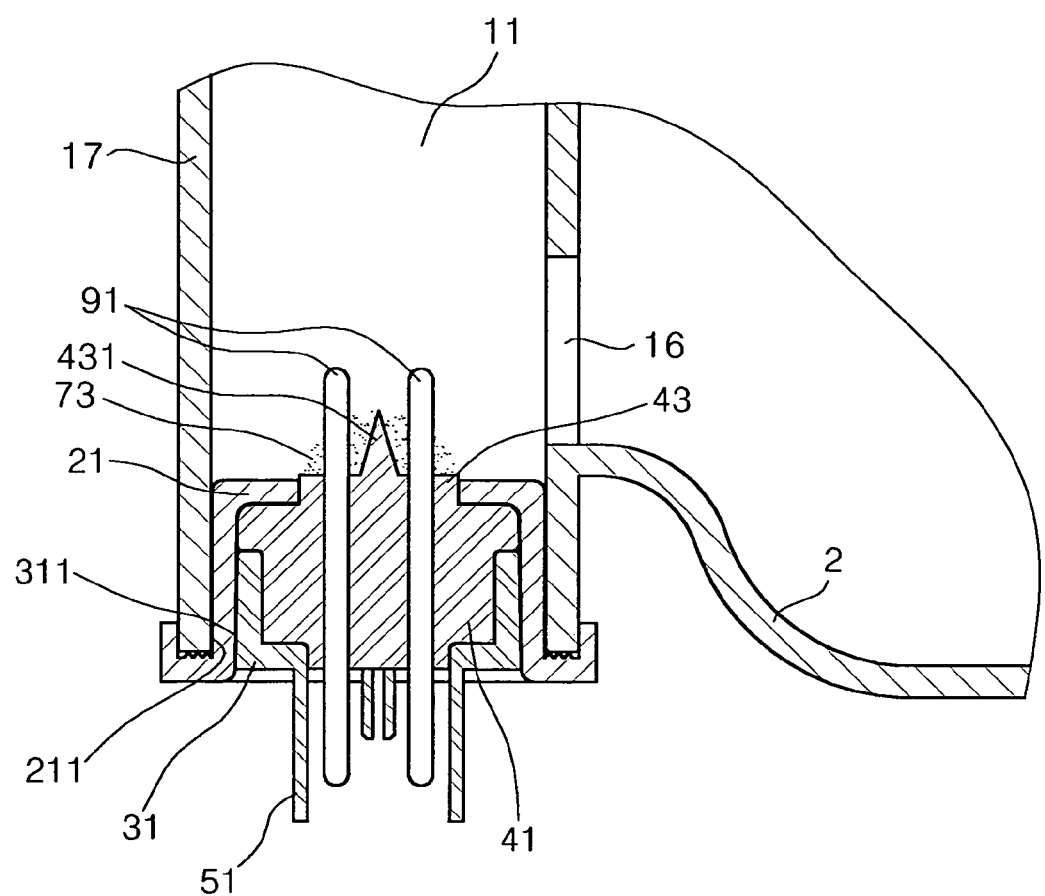
FIG. 7 is a sectional view of a conductivity sensor and an installation construction thereof according to a third embodiment of the present invention.
Figure 8:
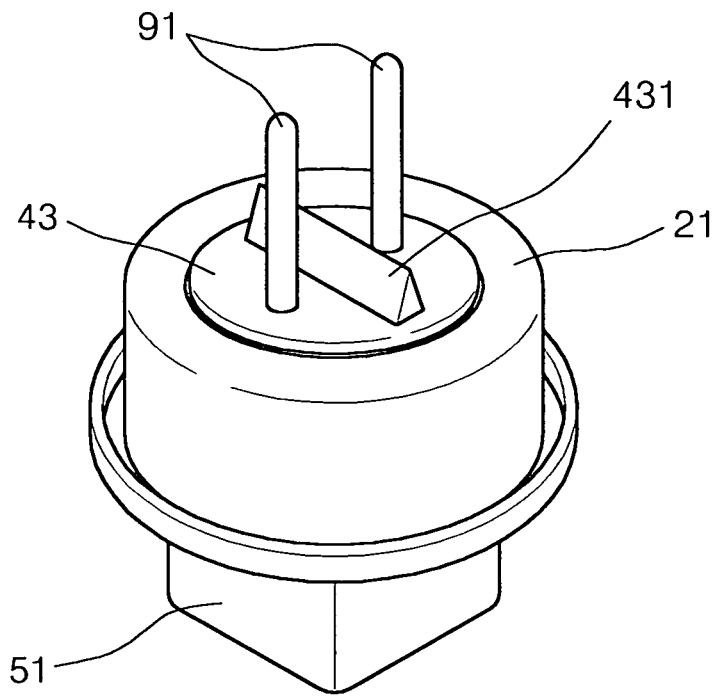
FIG. 8 is a perspective view of the conductivity sensor according to the third embodiment of the present invention.

A third embodiment of the present invention will be descried in detail with reference to FIGS. 7 and 8. The third embodiment provides a structure that can prevent an erroneous operation of the electrodes 91, which may be caused by foreign substance introduced inside a pneumatic chamber. The pneumatic chamber is formed in a hollow rod shape elongated upward and downward. Foreign substance, such as fluff or dirt, which is contained in the washing water, may be additionally introduced and stacked in an inside of the pneumatic chamber. If the foreign substance is intervened between the electrodes, the conductivity is changed abnormally, so that an amount of electric current is not sensed accurately. For example, if the foreign substance is intervened between the electrodes, it acts as a kind of conductor or nonconductor, so that an accurate measurement of the conductivity is not achieved. Accordingly, in this embodiment, a means for preventing the intervention of the foreign substance is further provided between the electrodes.

FIG. 7 is a sectional view of the conductivity sensor and an installation construction thereof according to the third embodiment of the present invention, and FIG. 8 is a perspective view of the conductivity sensor shown in FIG. 7.

Referring to FIGS. 7 and 8, the third embodiment of the present invention is mostly identical to the first and second embodiments described above. The conductivity sensor includes a pair of electrodes 91, an upper protection member 21, a lower protection member 31, a sealing member 41, an upper fixing portion 211, and a lower fixing portion 311. Further, the upper protection member 21 has an upper surface opened with a predetermined diameter and the electrodes 91 are protruded through the opening portion of the upper protection member 21. The sealing member 41 is protruded through the opening portion of the upper protection member 21 to thereby form an extended sealing part 43. Further, a shield member 431 is interposed at a central portion of the extended sealing part 43, specifically between the electrodes 91, to prevent foreign substance from being intervened between the electrodes 91.

In more detail, the shield member 431 is elongatedly formed in the central portion between the electrodes 91 to prevent the electric current from flowing through the lower portion of the electrodes 91.

Since the electric current flows between the electrodes 91, inorganic matters contained in the washing water may be precipitated on the upper surface of the upper protection member 21 by an oxidation-reduction reaction. If remnants are accumulated, an error may occur in a value of the electric current. Specifically, since the electric current flows through a shortest path, an error occurs in the measured value of the conductivity in a state that foreign substance 73 is intervened.

Accordingly, in order to prevent an occurrence of the error in the value of the electric current, which is caused by the precipitation of the foreign substance 73, the shield member 431 for shielding the lower portion of the electrodes 91 is previously formed protrudedly on the upper surface of the upper protection member 21 to thereby prevent the electric current from flowing through the lower end portion of the electrodes 91. Since a value of the conductivity measured through only the exposed portion of the electrodes 91 is different from that measured in case the entire electrodes 91 are exposed, the measured value is corrected in a process of converting it into a hardness value, thereby making it possible to measure a hardness value identical to a state that is not influenced by the precipitation of the foreign substance 73.

In addition, the shield member 431 is formed elongatedly at the central portion between the electrodes 91 in order to prevent the electric current on the electrodes 91 from flowing laterally. In order to prevent the precipitation of the foreign substance 73, the shield member 431 is formed narrowly in an upper direction. As constructed above, it is possible to prevent an occurrence of an error in the sensed value of the conductivity, which is caused by the foreign substance contained in the washing water. Specifically, it is possible to prevent the intervention of deformed organic/inorganic matters contained in the laundry or the detergent, which is put in the tub during the washing operation.

Meanwhile, the shield member 431 can be formed on the upper surface of the upper protection member 21. In addition, the foreign substance 73 can be discharged through the inlet/outlet port 16 during a drain cycle of the washing machine.

Fourth Embodiment

A fourth embodiment of the present invention will be described in detail with reference to FIGS. 9 to 11. The fourth embodiment of the present invention is mostly identical to the third embodiment described above. A difference is a detailed construction of the shield member and a method for forming the same.

Figure 9:
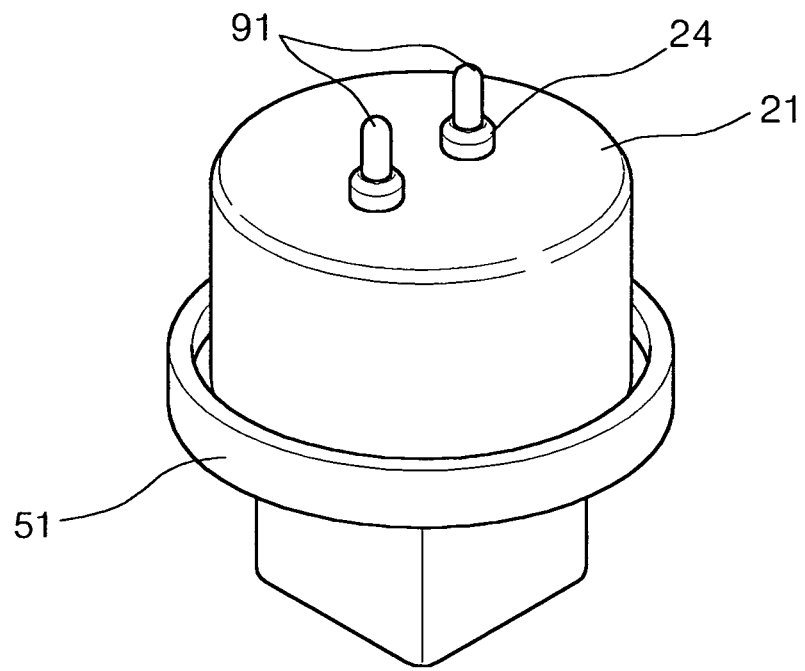
FIG. 9 is a perspective view of a conductivity sensor according to a fourth embodiment of the present invention.
Figure 10:
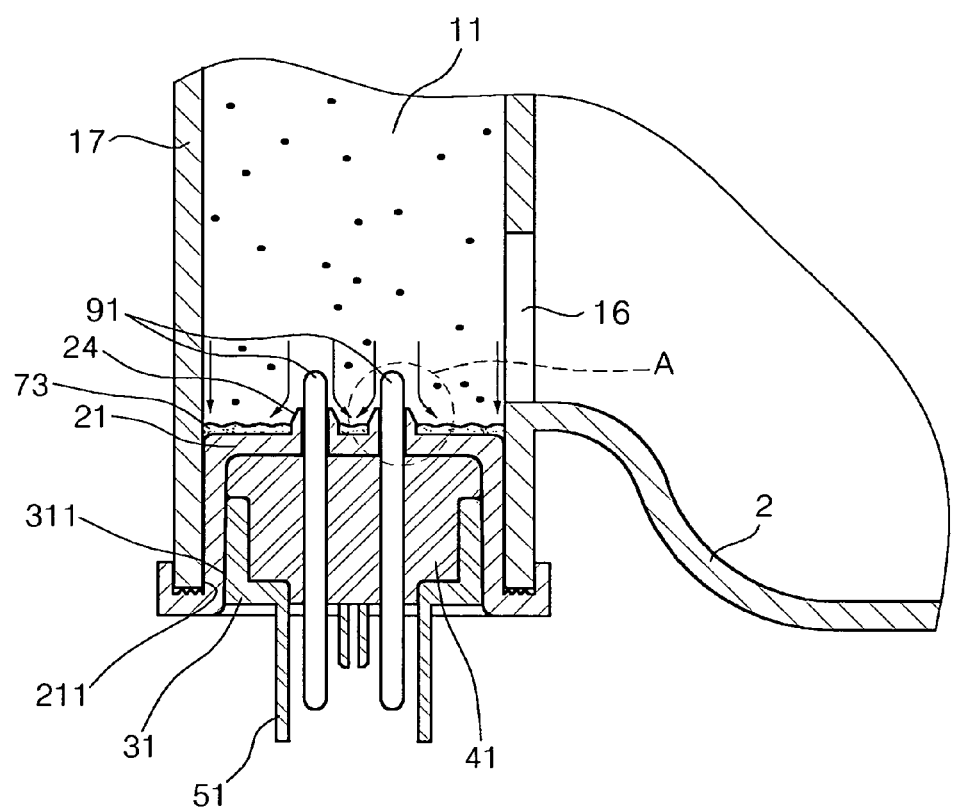
FIG. 10 is a sectional view of the conductivity sensor and an installation construction thereof according to the fourth embodiment of the present invention.

FIG. 9 is a perspective view of a conductivity sensor according to the fourth embodiment of the present invention, and FIG. 10 is a sectional view of the conductivity sensor shown in FIG. 9 and an installation construction thereof.

Referring to FIGS. 9 and 10, the conductivity sensor according to the fourth embodiment of the present invention includes a pair of electrodes 91, an upper protection member 21, a lower protection member 31, a sealing member 41 and an upper fixing portion 211 and a lower fixing portion 311, which are identical to those of the first embodiment described above. In addition, the conductivity sensor further includes a shield member 24 formed protrudedly around an outer periphery of the electrodes 91 on an upper surface of the upper protection member 21.

Specifically, the shield member 24 is protrudedly formed only on the outer periphery of the electrodes 91 as one body together with the upper protection member 21. In this manner, like the third embodiment, it is possible to prevent an error of the conductivity, which may be caused by the foreign substance 73.

Figure 11:
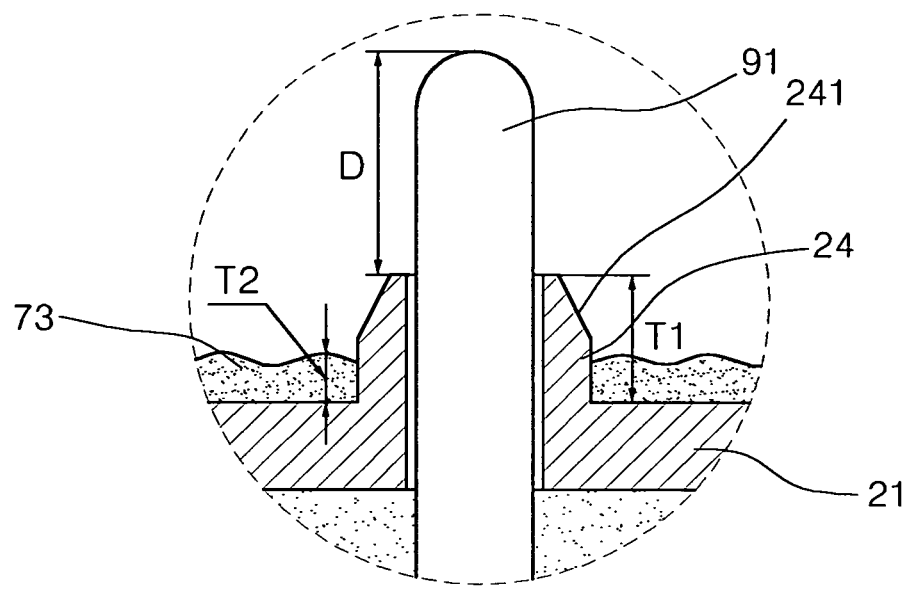
FIG. 11 is an enlarged sectional view of the portion "A" shown in FIG. 10.

FIG. 11 is an enlarged sectional view of the portion "A" shown in FIG. 10.

Referring to FIG. 11, the shield member 24 is formed with a predetermined height T1 in a vertical direction from the upper surface of the upper protection member 21 in order to enclose only a lower portion of the electrodes 91 protruded in the upper portion of the upper protection member 21. An upper portion of the shield member 24 is inclined at a predetermined slope, such that a diameter becomes smaller in an upper direction. As a result, an inclined surface 241 is formed.

In case foreign substance of the washing water contained in the pneumatic chamber 11 is precipitated, the foreign substance precipitated on the shield member 24 moves to edges along the inclined surface 241 and is then discharged out of the pneumatic chamber 11. Therefore, no precipitation layer is formed on the upper surface of the shield member 24.

Herein, an operation of the fourth embodiment of the present invention will be described below.

The foreign substance 73 is accumulated on the upper surface of the upper protection member 21 in a predetermined thickness T2. However, the protruded portion D of the electrode 91 is higher than a height T1 of the shield member 24.

The foreign substance 73 stacked on the upper protection member 21 is swept away together with the washing water during the drain cycle of the washing machine. Therefore, the foreign substance 73 is not stacked above the predetermined thickness T2 and does not influence the operation of the electrodes 91.

Further, in order to properly discharge the foreign substance 73, it is preferable that a lower height of the inlet/outlet port 16 is lower than at least an upper height of the upper protection member 21. In this manner, the foreign substance 73 can be eliminated more rapidly.

Fifth Embodiment

A fifth embodiment of the present invention will be described in detail with reference to FIGS. 12 and 13. The fifth embodiment of the present invention is mostly identical to the fourth embodiment described above. A difference is a construction of the shield member and a method for forming the same.

Figure 12:
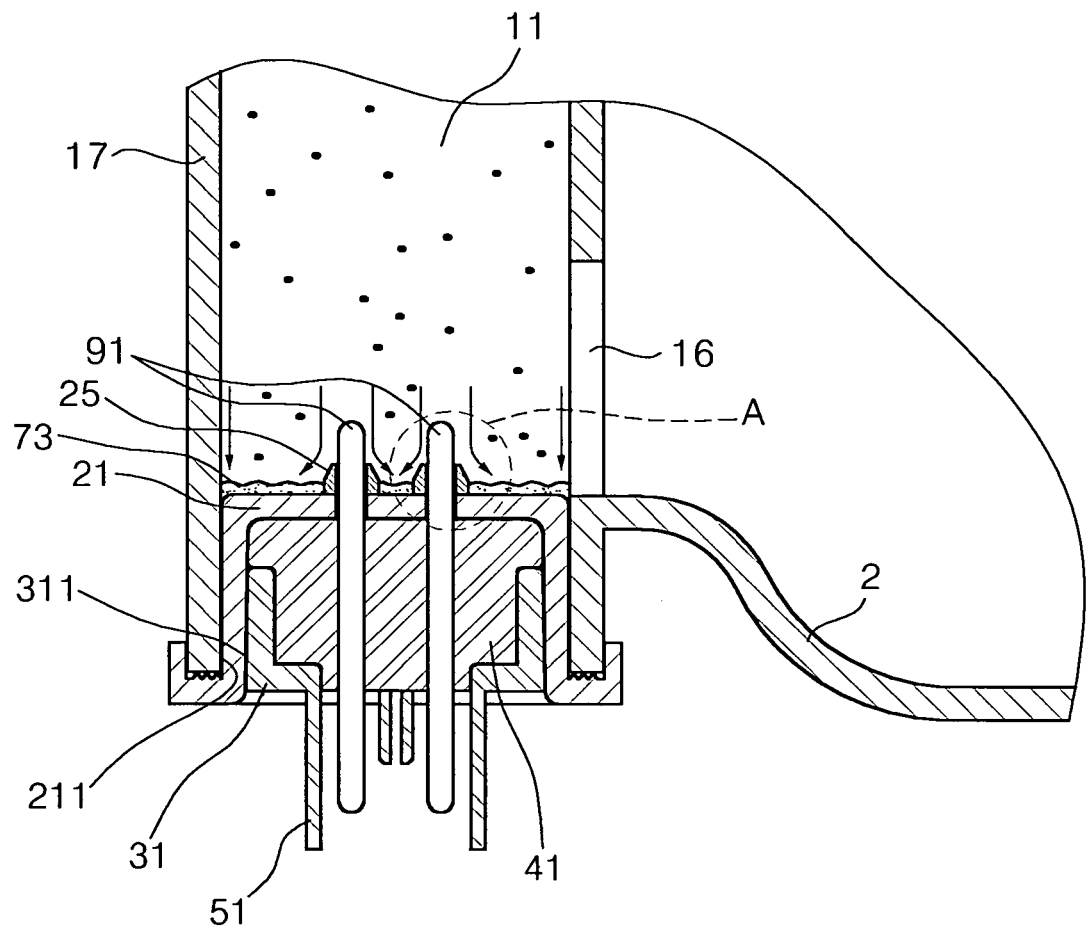
FIG. 12 is a sectional view of a conductivity sensor and an installation construction thereof according to a fifth embodiment of the present invention.
Figure 13:
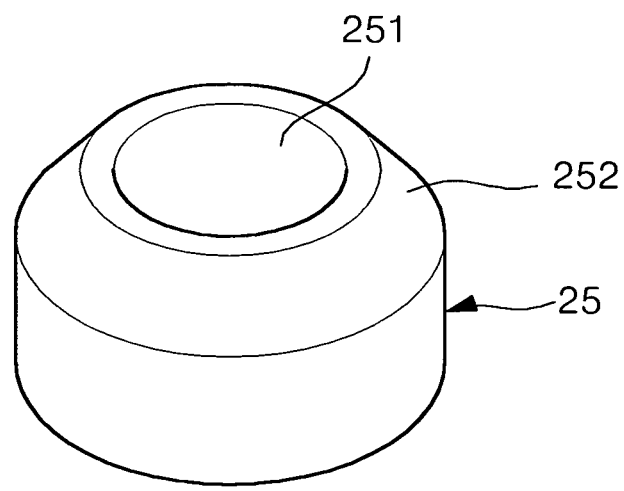
FIG. 13 is a perspective view of a shield member according to a fifth embodiment of the present invention.

FIG. 12 is a sectional view of a conductivity sensor and an installation construction thereof according to the fifth embodiment of the present invention, and FIG. 13 is a perspective view of the shield member shown in FIG. 12.

Referring to FIGS. 12 and 13, a difference between the fifth embodiment and the fourth embodiment is that the shield member is provided with a separate member. Specifically, the shield member 25 is provided with a member separated from the upper protection member 21 and mounted on a lower portion of the exposed electrode 91.

In more detail, the shield member 25 is formed in a cylinder shape. The shield member 25 includes an electrode inserting hole 251 opened at a central portion and through which one end portion of each electrode 91 insertedly passes, and an inclined surface 252 formed extendedly downward from the electrode inserting hole 251.

In case the shield member 25 is formed in the above manner, it is possible to obtain the same effect as the fourth embodiment described above.

Meanwhile, in this embodiment, the lower end portion of the inlet/outlet port 16 is formed equal to or lower than the upper position of the upper protection member 21, such that the foreign substance can be discharged more smoothly during the drain cycle of the washing machine.

Sixth Embodiment

A sixth embodiment of the present invention will be described in detail with reference to FIGS. 14 and 15. The sixth embodiment of the present invention is characteristic of a method for coupling the upper and lower protection members for protecting the electrodes and a method for forming a temperature sensor together with the electrodes.

Figure 14:
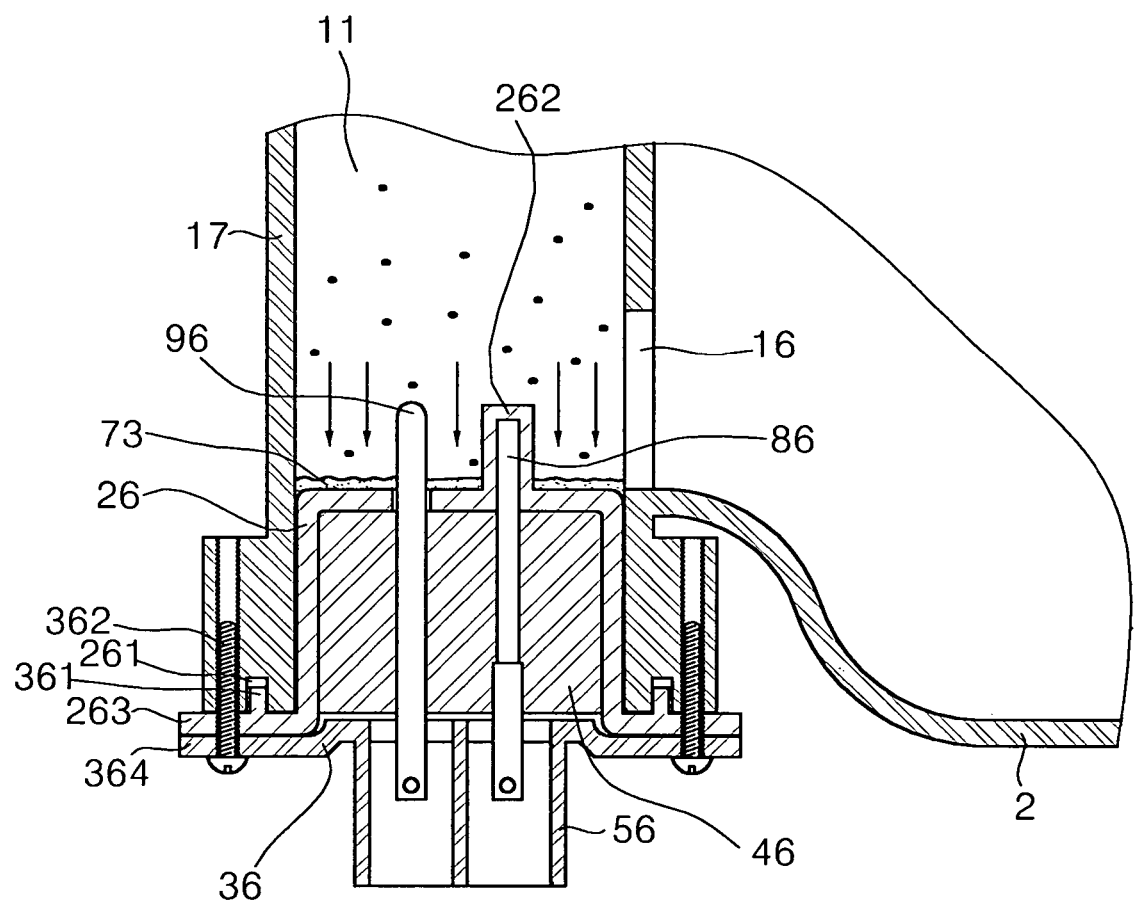
FIG. 14 is a sectional view of a conductivity sensor and an installation construction thereof according to a sixth embodiment of the present invention.
Figure 15:
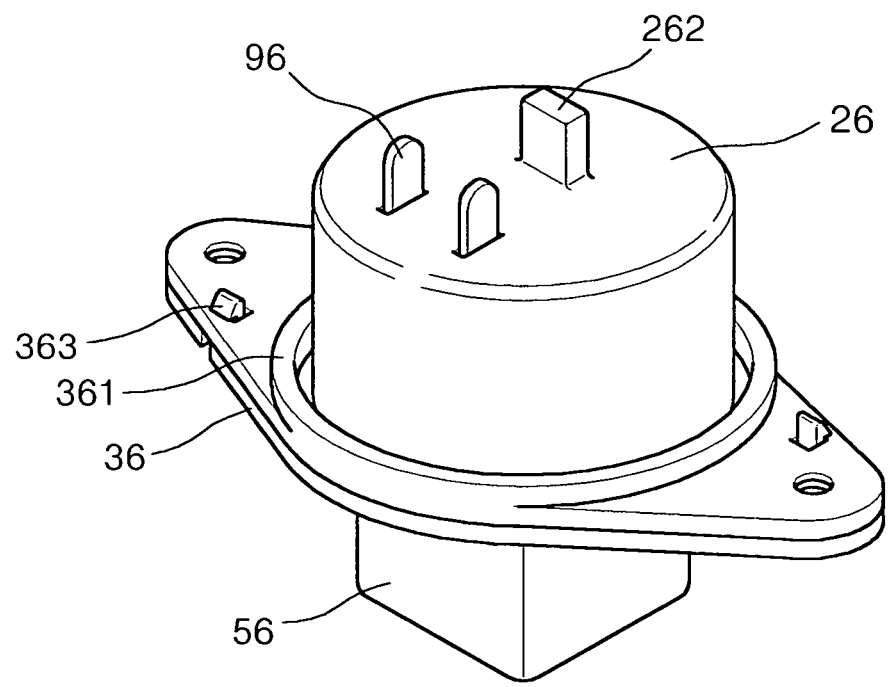
FIG. 15 is a perspective view of the conductivity sensor according to the sixth embodiment of the present invention.

FIG. 14 is a sectional view of a conductivity sensor and an installation construction thereof according to the sixth embodiment of the present invention, and FIG. 15 is a perspective view of the conductivity sensor shown in FIG. 14.

Referring to FIGS. 14 and 15, the conductivity sensor according to the sixth embodiment of the present invention includes a pair of electrodes 96, an upper protection member 26, a lower protection member 36 and a sealing member 46, which are identical to those of fifth embodiment described above. A difference is that a temperature sensor 86 is further formed to measure a water temperature. The conductivity sensor according to the sixth embodiment of the present invention is characteristic of a coupling structure between the upper protection member 26 and the lower protection member 36 and a coupling structure between the conductivity sensor and the chamber housing 17.

Specifically, the temperature sensor 86 is formed in the same manner as the conductivity sensor. The temperature sensor 86 is protected by a temperature sensor protection part 286, which is formed as one body together with the upper protection member 26 and sealed. Since the temperature sensor 86 has only to measure a temperature of the washing water, it need not directly contact with the washing water. In addition, the temperature sensor 86 has only to measure a temperature using a calorie transmitted through the temperature sensor protection part 262.

The conductivity sensor further includes an upper flange 263 extended from the lower end portion of the upper protection member 26, a lower flange 364 arranged with the upper flange 263, and a coupling member 362 passing through the upper and lower flanges 263 and 364 and being inserted up to the chamber housing 17.

Further, a latch 363 is inserted into a predetermined hole formed at the upper flange 263 in order for a provisional assembly of the upper and lower protection members 26 and 36.

In order to correctly fit the provisionally assembled conductivity sensor into the chamber housing 17, a fitting guide 361 is protrudedly formed upward on the upper flange 263 and a guide groove 261 is arranged with the fitting guide 361.

In addition, the temperature sensor 86 and the electrodes 96 may be formed in a flat shape, not a circular bar shape. Of course, a predetermined connector 56 to which a power terminal is connected is further formed downward from the lower protection member 36.

Herein, an operation of the sixth embodiment will be described below.

In a state that the electrodes 96 and the temperature sensor 86 are placed, a liquid sealant for the sealing member 46 is injected to fix a position of the sealing member 46. At this time, the temperature sensor 86 does not directly contact with the washing water and is sealed with the temperature sensor protection part 262 formed as one body together with the upper protection member 26, such that the temperature sensor 86 is protected.

Then, the upper flange 263 extended at the lower end portion of the upper protection member 26 and the lower flange 364 extended at the outer periphery of the lower protection member 36 are arranged in a row and coupled with each other. In other words, the latch 363 protruded upward from the lower flange 364 is inserted into the predetermined hole formed at the upper flange 263 to thereby fix the upper and lower protection members 26 and 36. As a result, the upper and lower flanges 263 and 364 can be assembled provisionally. The provisionally assembled protection members 26 and 36 can be placed at a predetermined position in the lower end portion of the chamber housing 17 in a state that the fitting guide 361 is guided by the guide groove 261. The positioned protection members 26 and 36 are firmly fixed and sealed at the opened lower portion of the chamber housing 17 by means of the coupling member 362 passing through the protection members 26 and 36 and the chamber housing 17.

Since the process of measuring the conductivity in a state that the conductivity sensor is fixed is identical to that described above, a detailed description will be omitted. The water temperature measured by the temperature sensor 86 can be used as a factor that determines an amount of the washing water. For example, in case the temperature of the washing water is high, an activity of the detergent is high such that a small amount of detergent is inputted. Meanwhile, in case the temperature of the washing water is low, an activity of the detergent is low such that a large amount of detergent is inputted in order to obtain the same washing efficiency.

Seventh Embodiment

A seventh embodiment of the present invention will be described in detail with reference to FIGS. 16 and 17. The seventh embodiment of the present invention is mostly identical to the sixth embodiment described above. A difference is an additional construction for rapidly discharging foreign substance accumulated inside the pneumatic chamber 11.

Figure 16:
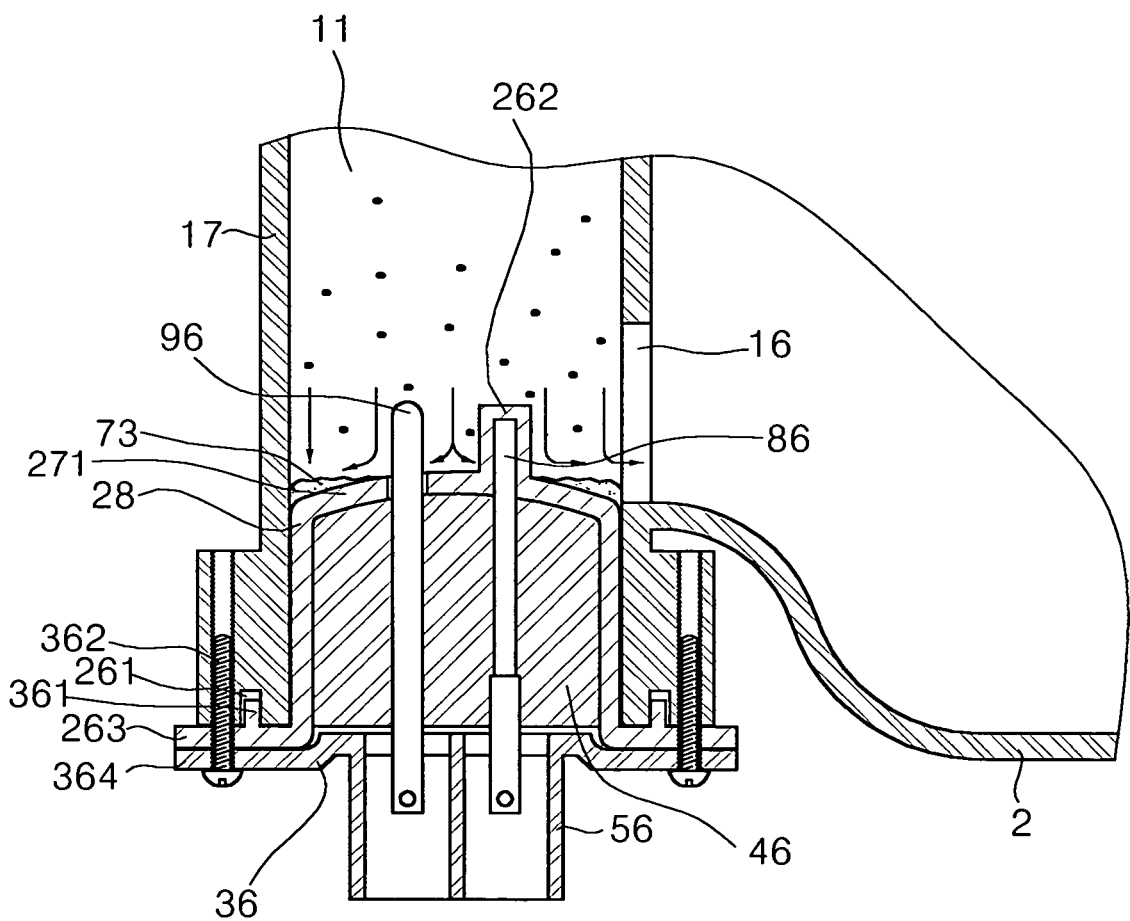
FIG. 16 is a sectional view a conductivity sensor and an installation construction thereof according to a seventh embodiment of the present invention.
Figure 17:
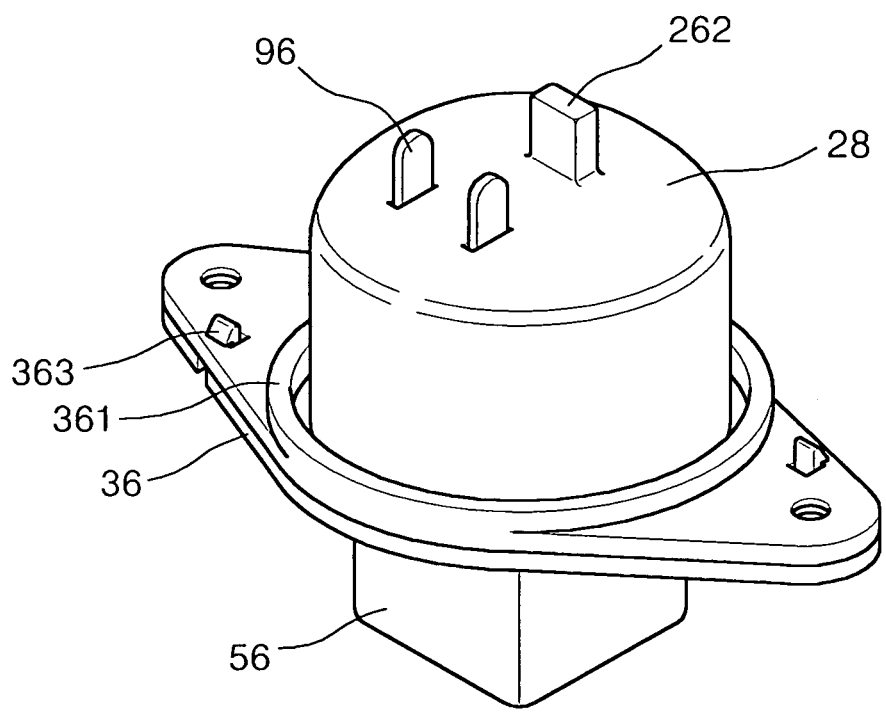
FIG. 17 is a perspective view of the conductivity sensor according to the seventh embodiment of the present invention.

FIG. 16 is a sectional view of a conductivity sensor and an installation construction thereof according to the seventh embodiment of the present invention, and FIG. 17 is a perspective view of the conductivity sensor shown in FIG. 16.

Referring to FIGS. 16 and 17, an upper surface of the upper protection member 26 is formed convexly to provide a guide part 271 along which foreign substance moves. The foreign substance 73 accumulated inside the pneumatic chamber 11 moves toward an edge of the upper protection member 26 along the guide part 271 due to its own weight. While the washing water is being discharged, the foreign substance 73 can be discharged through the inlet/outlet port 16 together with the washing water. At this time, it is preferable that a lower end portion of the inlet/outlet port 16 has a height lower than the edge of the upper protection member 26.

This embodiment of the present invention has an effect that the conductivity can be measured without any influence of the foreign substance.

Eighth Embodiment

An eighth embodiment of the present invention will be described in detail with reference to FIGS. 18 to 20. The eighth embodiment of the present invention is mostly identical to the seventh embodiment described above. A difference is an additional construction for preventing the electrodes and the temperature sensor from being vibrated. A vibration continuously occurs in the washing machine due to a driving of the motor and causes the positions of the electrodes and the temperature sensor to be changed. Further, due to the vibration, a contact point may be disconnected. This embodiment is provided for solving these problems.

Figure 18:
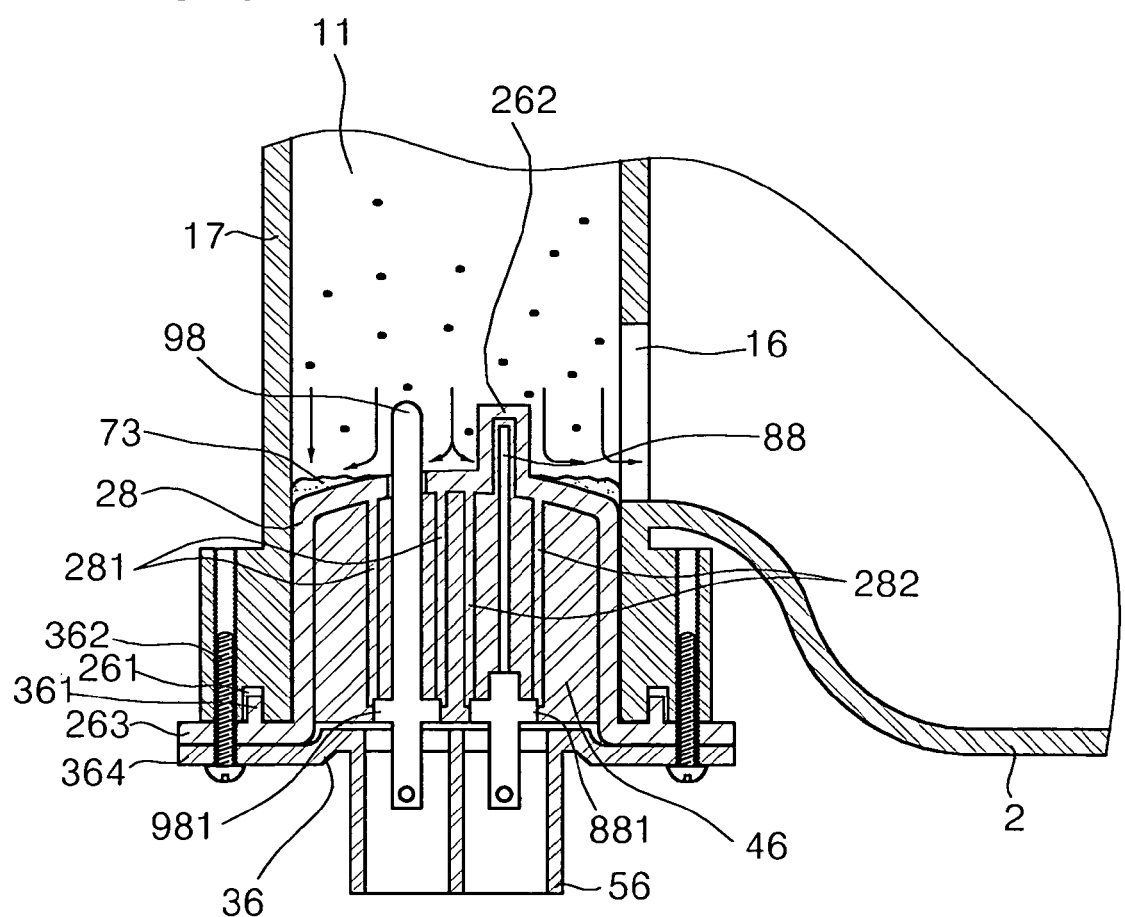
FIG. 18 is a sectional view of a conductivity sensor and an installation construction thereof according to an eighth embodiment of the present invention.
Figure 19:
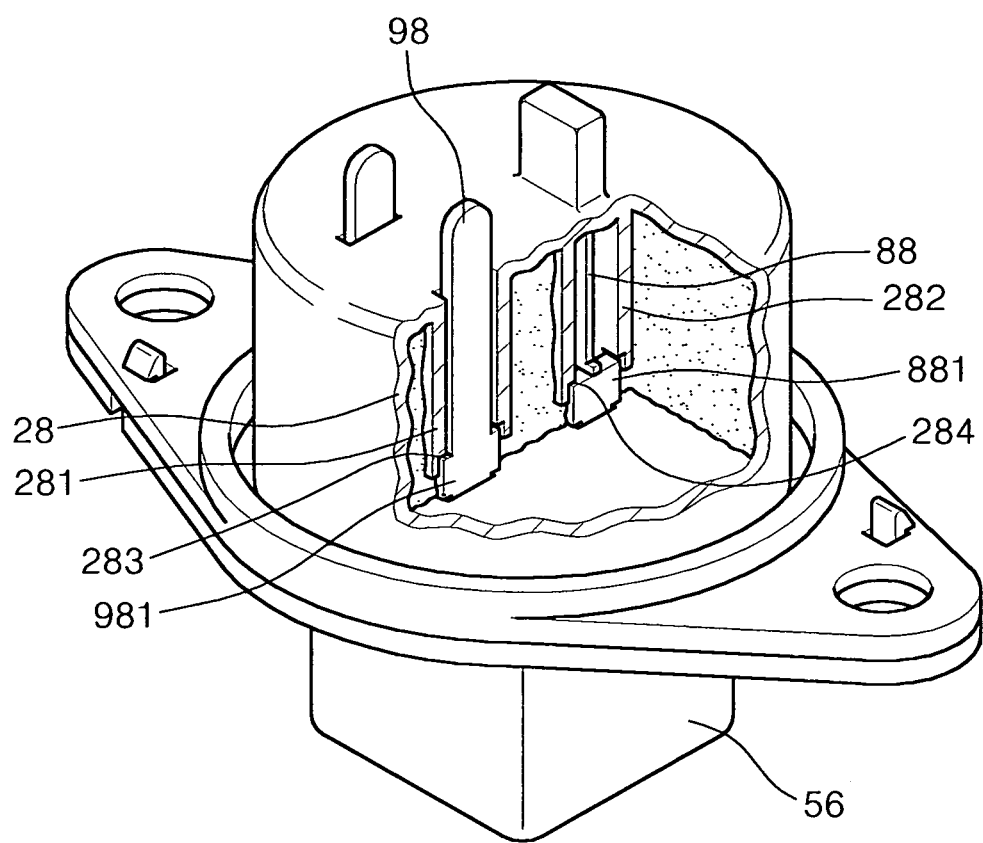
FIG. 19 is a perspective view of the conductivity sensor according to the eight embodiment of the present invention, which is partially broken away.

FIG. 18 is a sectional view of a conductivity sensor and an installation construction thereof according to the eighth embodiment of the present invention, and FIG. 19 is a perspective view showing a portion of the electrodes, which is partially broken away.

Referring to FIGS. 18 and 19, the conductivity sensor according to the eighth embodiment of the present invention includes a pair of electrodes 98, an upper protection member 28, a lower protection member 36, a sealing member 46, a temperature sensor 88, a temperature sensor protection part 262, an upper flange 263, a lower flange 364, a coupling member 362, a latch 363, a fitting guide 361, a guide groove 261, and a connector 56, which are almost identical to those of the seventh embodiment described above.

In this embodiment, the conductivity sensor further includes an electrode support rib 281 extended downward in the inside of the upper protection member 28 and a temperature sensor support rib 282 extended downward in the inside of the upper protection member 28 in the same manner as the electrode support rib 281. In the electrode support rib 281 and the temperature sensor support rib 282, a sealing member 46 is filled between the electrodes 98 and the temperature sensor 88. Therefore, even though some portion of the sealing member 46 is broken, the sealing member 46 is not damaged entirely. When the electrodes 98 and the temperature sensor 88 are vibrated, a propagation of the vibration is stopped due to the respective support ribs 281 and 282. As a result, the vibrations of the electrodes 98 and the temperature sensor 88 can be prevented. Further, it is possible to enhance a vibration resistance of the sealing member 46. Specifically, the electrode support rib 281 and the temperature sensor support rib 282 cause the electrodes 98 and the temperature sensor 88 to endure the vibration applied in a right and left direction.

Additionally, the conductivity sensor further includes an electrode protrusion 981 formed protrudedly at a predetermined position of the electrode 98 and a temperature sensor protrusion 881 formed protrudedly at a predetermined position of the temperature sensor 88.

Further, positions of the upper and lower end portions of the electrode protrusion 981 are supported by the electrode support rib 281 and the lower protection rib 36, respectively. Therefore, it is possible to prevent the up and down vibration of the electrodes 98, which is caused by the vibration externally applied up and down. Similarly, positions of the upper and lower end portions of the temperature sensor protrusion 881 are supported by the temperature sensor support rib 282 and the lower protection member 36, respectively. Therefore, it is possible to prevent the up and down vibration of the temperature sensor 88, which is caused by the vibration externally applied up and down. In this manner, since the electrodes 98 and the temperature sensor 88 are prevented from being vibrated, the damage of the sealing member 46 can be prevented, thereby improving the performance of the sealing member 46. As a result, the reliability of the sealing can also be improved.

Meanwhile, an electrode fitting groove 283 formed by depressing an end portion of the electrode support rib 281 is provided at a position where the electrodes 98 and the electrode support rib 281 contact with each other, and a temperature sensor fitting groove 284 formed by depressing an end portion of the temperature sensor support rib 282 is provided at a position where the temperature sensor 88 and the temperature sensor support rib 282 contact with each other. Consequently, the electrodes 98 and the temperature sensor 88 can be fitted into accurate positions and supported firmly.

Figure 20:
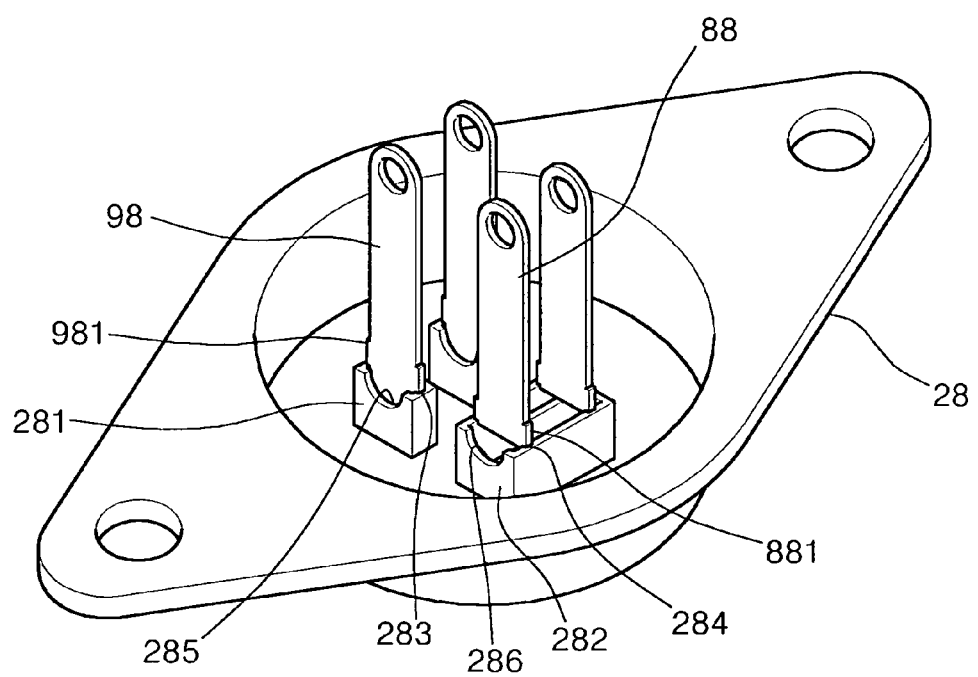
FIG. 20 is a perspective view showing a lower portion of electrodes and a temperature sensor fitted into an upper protection member according to the eighth embodiment of the present invention.

FIG. 20 is a perspective view showing a lower portion of the electrodes and the temperature sensor fitted into the upper protection member according to the eighth embodiment of the present invention.

Referring to FIG. 20, the electrode support rib 281 and the temperature sensor support rib 282, which are extended from the lower portion of the upper protection member 28, are protrudedly formed in a rectangular shape. The electrodes 98 and the temperature sensor 88 are fitted into the fitting grooves 283 and 284 formed inside the support ribs 281 and 282. Specifically, an electrode protrusion 981 and a temperature sensor protrusion 881 are internally inserted and fitted into the grooves 283 and 284.

Meanwhile, in the electrode support rib 281 and the temperature sensor support rib 282, sealant injection grooves 285 and 286 are formed at another portion where the fitting grooves 283 and 284 are not formed in order for smoothly injecting the liquid sealant among the support ribs 281 and 282, the electrodes 98 and the temperature sensor 88. The sealant injection grooves 285 and 286 allow the liquid sealant to be injected smoothly. In addition, the sealing member 46 formed after the sealant is injected and solidified can support the electrodes 98 and the temperature sensor 88 more firmly.

The reason why the temperature sensor 88 is branched into two pieces at the lower portion is to secure the reliability of signal transmission and support the sealing member 46 firmly. At this time, the temperature sensor 88 can also be branched into one piece.

This embodiment can prevent the vibration of the electrodes and the temperature sensor themselves and due to the external impact. Additionally, since the electrodes and the temperature sensor are not vibrated, there is nothing to worry about the disconnection of the respective contact points. Further, the reliability of the product can be improved much more.

Ninth Embodiment

A ninth embodiment of the present invention will be described in detail with reference to FIGS. 21 to 23. This embodiment is characterized in that a specific structure is further formed in order to prevent the electrodes and the temperature sensor from being vibrated.

Figure 21:
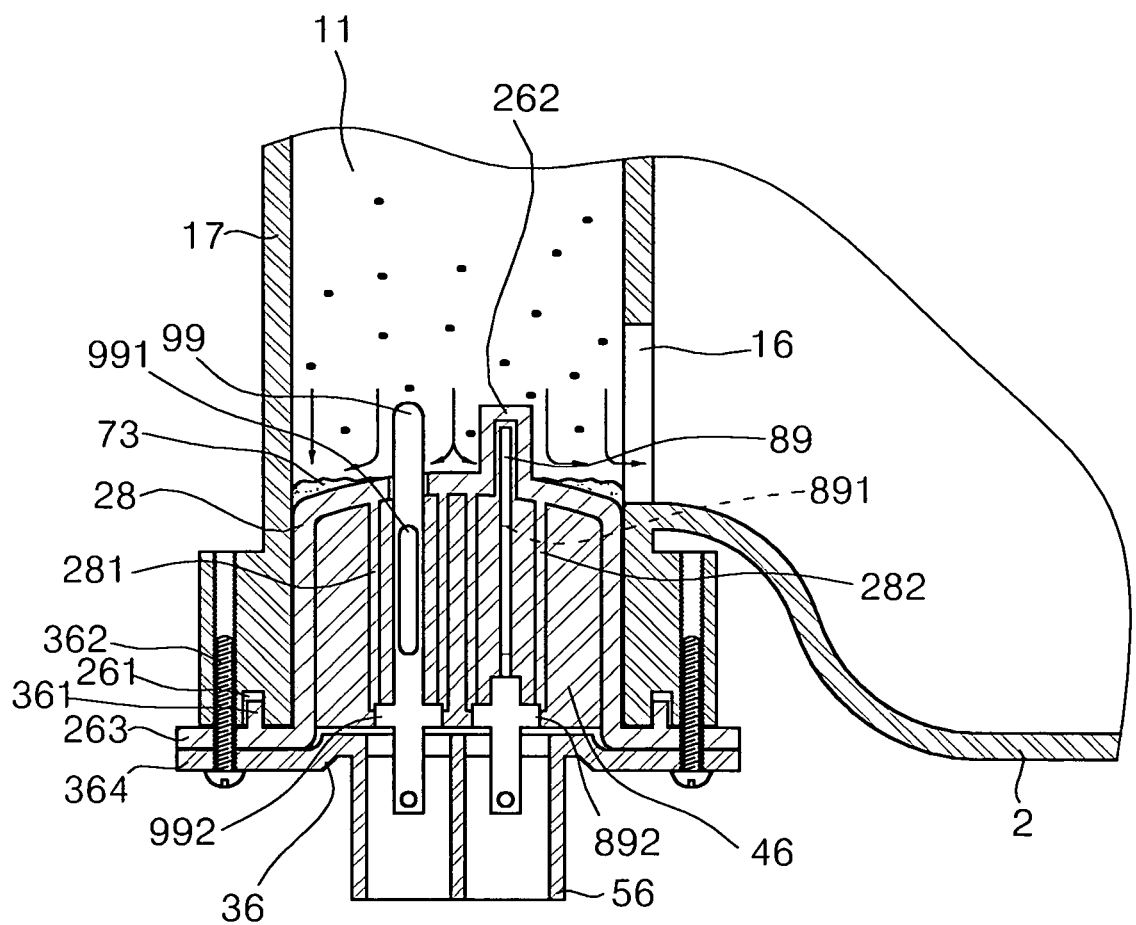
FIG. 21 is a sectional view of a conductivity sensor and an installation construction thereof according to a ninth embodiment of the present invention.
Figure 22:
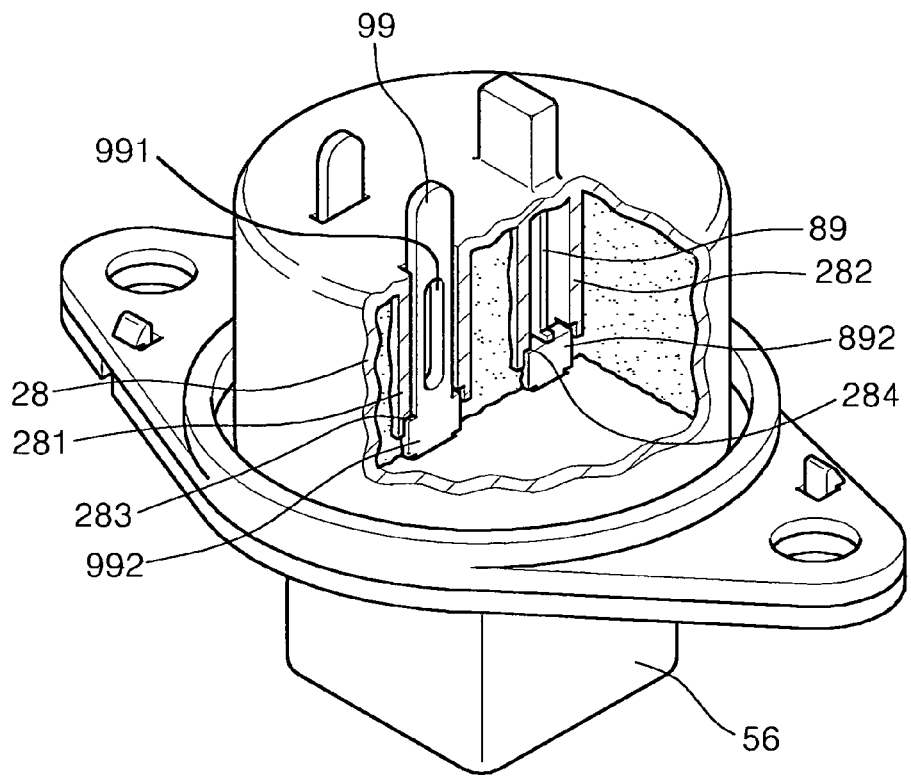
FIG. 22 is a perspective view of the conductive sensor according to the ninth embodiment of the present invention, which is partially broken away.

FIG. 21 is a sectional view of a conductivity sensor and an installation construction thereof according to the ninth embodiment of the present invention, and FIG. 22 is a perspective view of the conductivity sensor according to the ninth embodiment of the present invention, which is partially broken away.

Referring to FIGS. 21 and 22, this embodiment of the present invention is mostly identical to the eighth embodiment described above. A difference is a topology of the electrodes 99 and the temperature sensor 89. In other words, a predetermined hole is formed at each body of the electrode 99 and the temperature sensor 89.

Specifically, each of the electrodes 99 includes: an electrode protrusion 992 formed at a predetermined position of a bar-shaped body to support the position of the electrode; and an electrode fixing hole 991 formed by opening a predetermined position of the body of the electrode 99. Like the electrodes 99, the temperature sensor 89 includes: a temperature sensor protrusion 892 formed at a predetermined position of a bar-shaped body to support the position of the temperature sensor; and a temperature sensor fixing hole 891 formed by opening a predetermined position of the body of the temperature sensor 89.

The construction and operation of the electrode protrusion 992 and the temperature sensor protrusion 892 are identical to those of the eighth embodiment described above. Herein, the operations of the electrode fixing hole 991 and the temperature sensor fixing hole 891 will be described below. A liquid sealant for the sealing member is injected and solidified in the inside of the electrode fixing hole 991 and the temperature sensor fixing hole 891. The liquid sealant is injected up to the insides of the electrode fixing hole 991 and the temperature sensor fixing hole 891 and then solidified. By doing so, the sealant arrives at a wider area and is then solidified, such that the positions of the electrodes 99 and the temperature sensor 89 are supported more reliably by the solidified sealing member 46.

Figure 23:
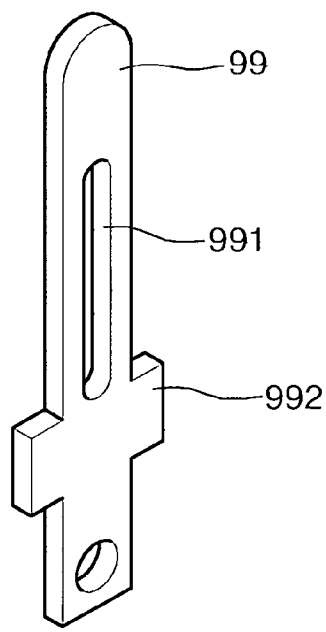
FIG. 23 is a perspective view of an electrode according to the ninth embodiment of the present invention.

FIG. 23 is a perspective view of the electrode according to the ninth embodiment of the present invention.

Referring to FIG. 23, each of the electrodes 99 consists of a main body formed in a flat shape and a width of the electrode is expanded at a predetermined portion. In this manner, the electrode protrusion 992 for supporting the position of the electrodes 99 is formed. Additionally, the electrode fixing hole 991 in which the sealing member 46 is formed up to the predetermined opened portion is formed in the body of the electrode. Of course, the temperature sensor 89 can be formed with the same structure as the electrodes 99. Although the formations of the electrode fixing hole 991 and the temperature sensor fixing hole 891 are described in this embodiment, grooves can be formed instead of the holes because it is essential to seal much wider area in the main body.

Tenth Embodiment

A tenth embodiment of the present invention will be described in detail with reference to FIGS. 24 to 28. The tenth embodiment of the present invention is mostly identical to the eighth embodiment described above. A difference is a construction of a connector and a receptacle for transferring an amount of electricity, sensed by the electrodes and the temperature sensor, through a wire.

Figure 24:
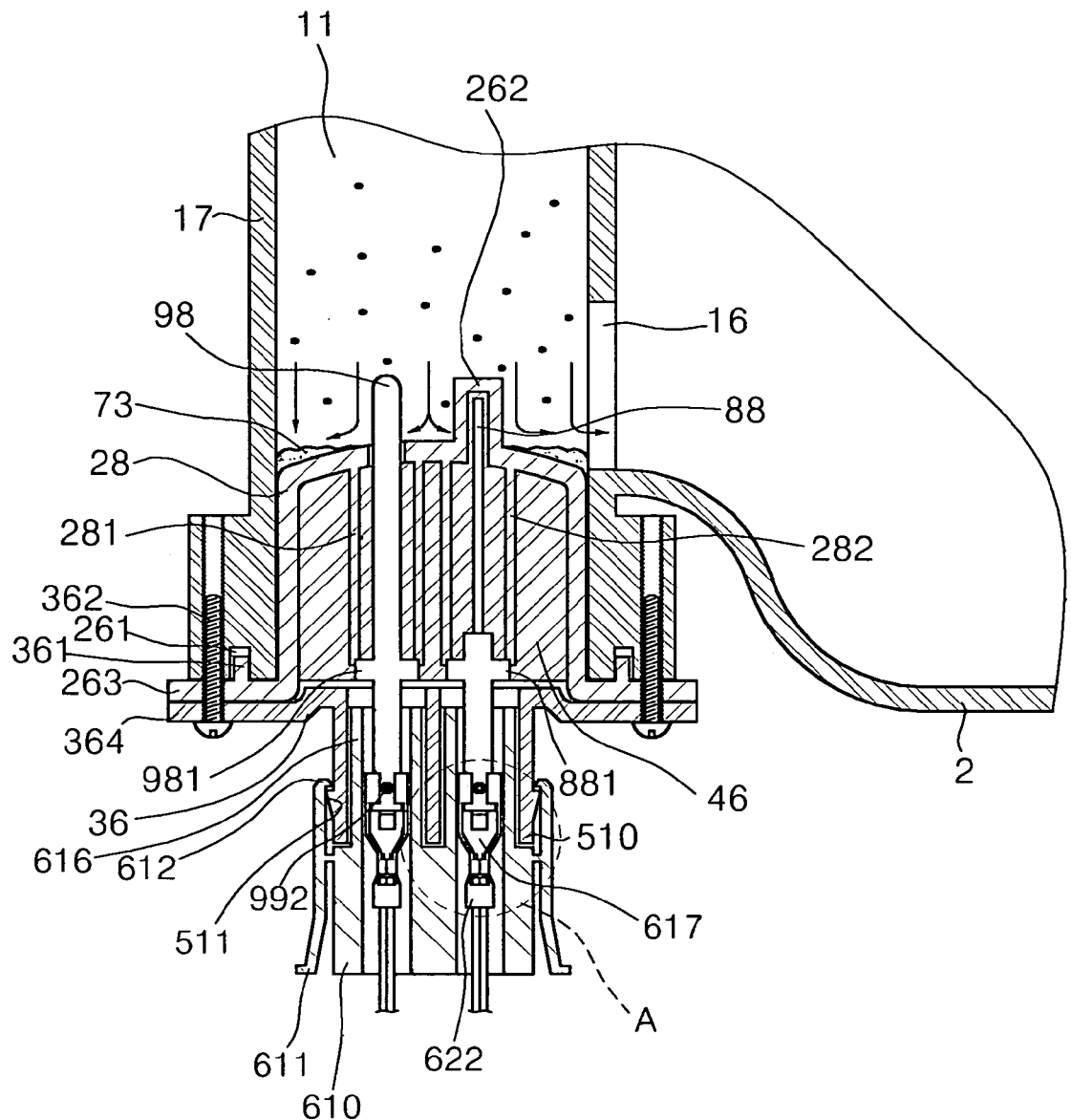
FIG. 24 is a sectional view of a conductivity sensor and an installation construction thereof according to a tenth embodiment of the present invention.
Figure 25:
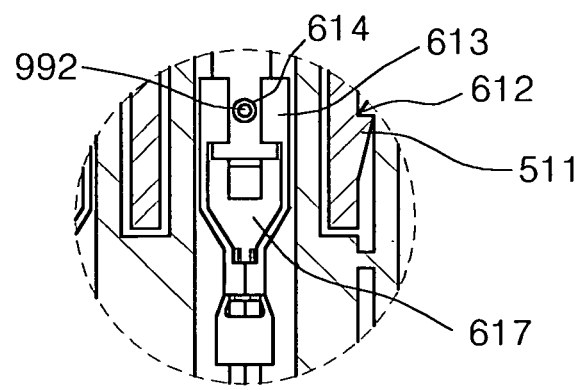
FIG. 25 is an exploded view of the portion "A" shown in FIG. 24.
Figure 26:
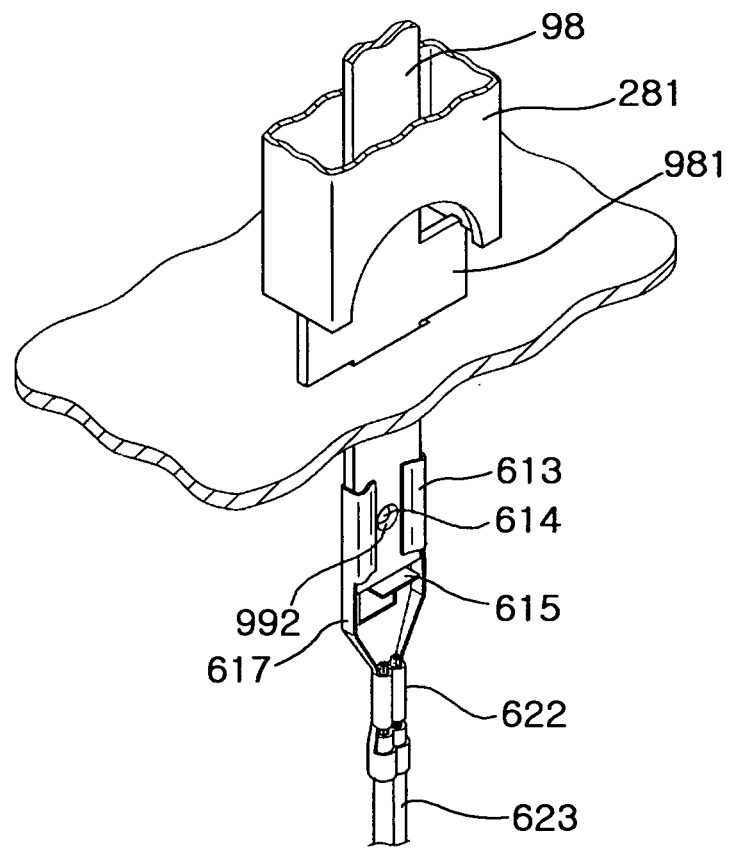
FIG. 26 is a perspective view showing a coupling portion between a connector and a receptacle according to the tenth embodiment of the present invention.

FIG. 24 is a sectional view of a conductivity sensor and an installation construction thereof according to the tenth embodiment of the present invention, FIG. 25 is an enlarged view of the portion "A" shown in FIG. 24, and FIG. 26 is a perspective view of a coupling portion between a connector and a receptacle according to the present invention.

Referring to FIGS. 24 and 25, the conductivity sensor according to the tenth embodiment of the present invention includes a pair of electrodes 98, an upper protection member 28, a lower protection member 36, a sealing member 46, a temperature sensor 88, a temperature sensor protection part 262, an upper flange 263, a lower flange 364, a coupling member 362, a latch 363, a fitting guide 361, and a guide groove 261, which are almost identical to those of the eighth embodiment described above. A difference is that the conductivity sensor further includes a connector 510 extended downward from the lower protection member 36 and a receptacle 610 inserted into the connector 510.

In other words, the conductivity sensor includes: a latch protrusion 511 formed protrudedly from an outer periphery of the connector 510; guide holes 992 formed at lower end portions of the electrodes 98 and the temperature sensor 88 in an inside of the connector 510; a receptacle handle 611; a fixing protrusion 612 formed an outer periphery of the receptacle 610 and caught by the latch protrusion 511, in which the fixing protrusion 612 can perform a predetermined elastic restoring motion due to an external force applied by a user;

and a position manipulating part 616 inserted in contact with an inner periphery of the connector 510 to allow a clear motion of the receptacle.

Herein, the operation of the connector 510 and the receptacle 610 will be described below with reference to FIG. 26. The plate member of a conductive material is deformed to form a conductive member 617 in an inside of the receptacle 610. The receptacle includes: a wire fixing part 622 formed at one end portion of the conductive member 617 to hold the wire 623; an inserting part 613 foldedly formed on an opposite side of the wire fixing part 622 provided for an electrical connection at the end portions of the electrodes 98 and the temperature sensor 88; a fitting protrusion 614 fitted in arrangement with the guide hole 992 so that the inserted conductive member cannot be released; and a stopper 615 provided for preventing an excessive insertion of the conductive member 617 after a predetermined length of the conductive member 617 is inserted into the connector 510, in which the conductive member 617 is stopped due to the lower end portions of the electrodes 98 and the temperature sensor 88.

Accordingly, if the receptacle 610 and the conductive member 617 are inserted as much as a predetermined depth, the fitting protrusion 614 is fitted into the guide hole 992, and the stopper 615 reaches the lower end portions of the electrodes 98 and the temperature sensor 88 and is not inserted any longer. Additionally, the fixing protrusion 612 is caught by the latch protrusion 511, so that it is not released if the user does not apply an external force. As a result, three coupling structures apply a coupling force at the same time. Therefore, even though an external vibration occurring during an operation of the washing machine is applied, the structures of the connector and the receptacle which respectively act as the input and output terminals of electrical signals are not weakened, so that the connector and the receptacle are not released.

Figure 27:
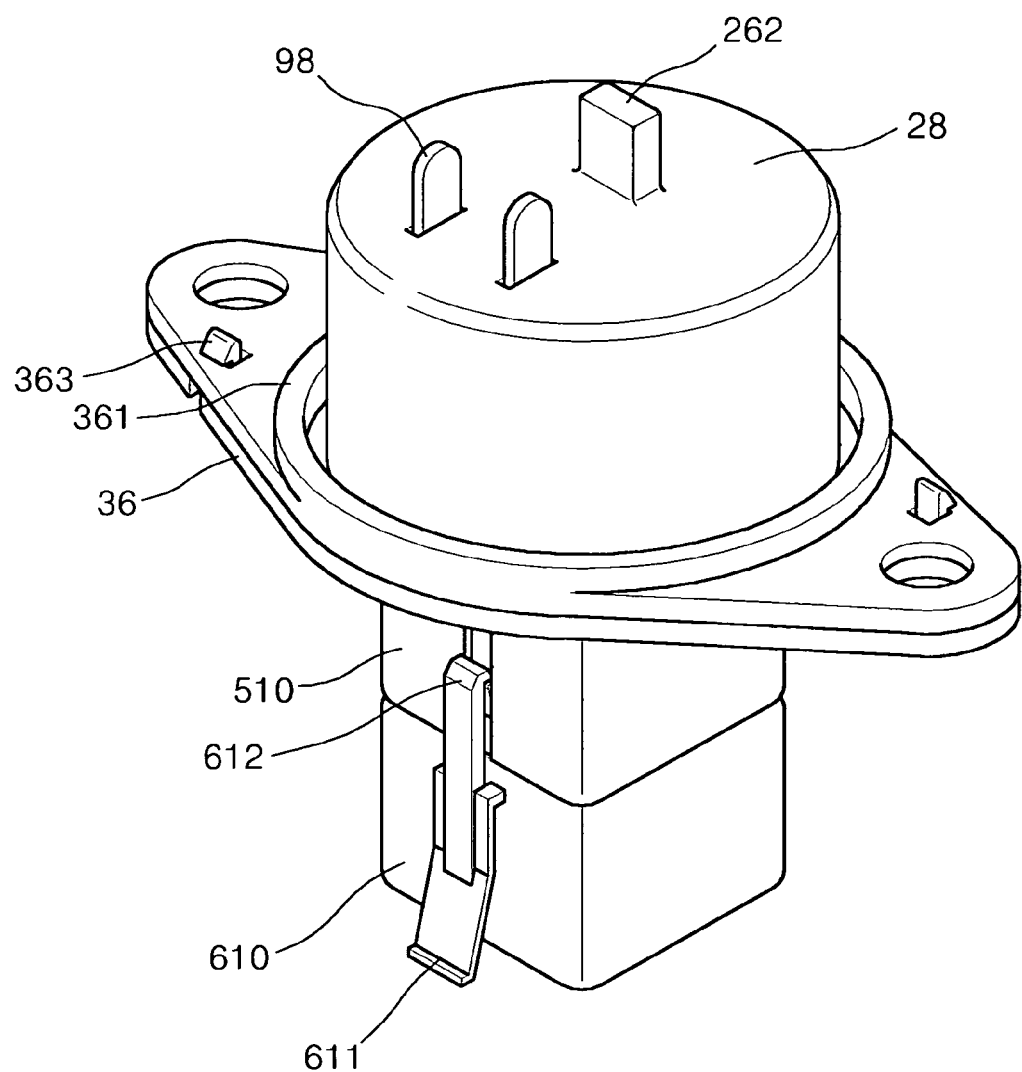
FIG. 27 is a perspective view of the conductivity sensor according to the tenth embodiment of the present invention.
Figure 28:
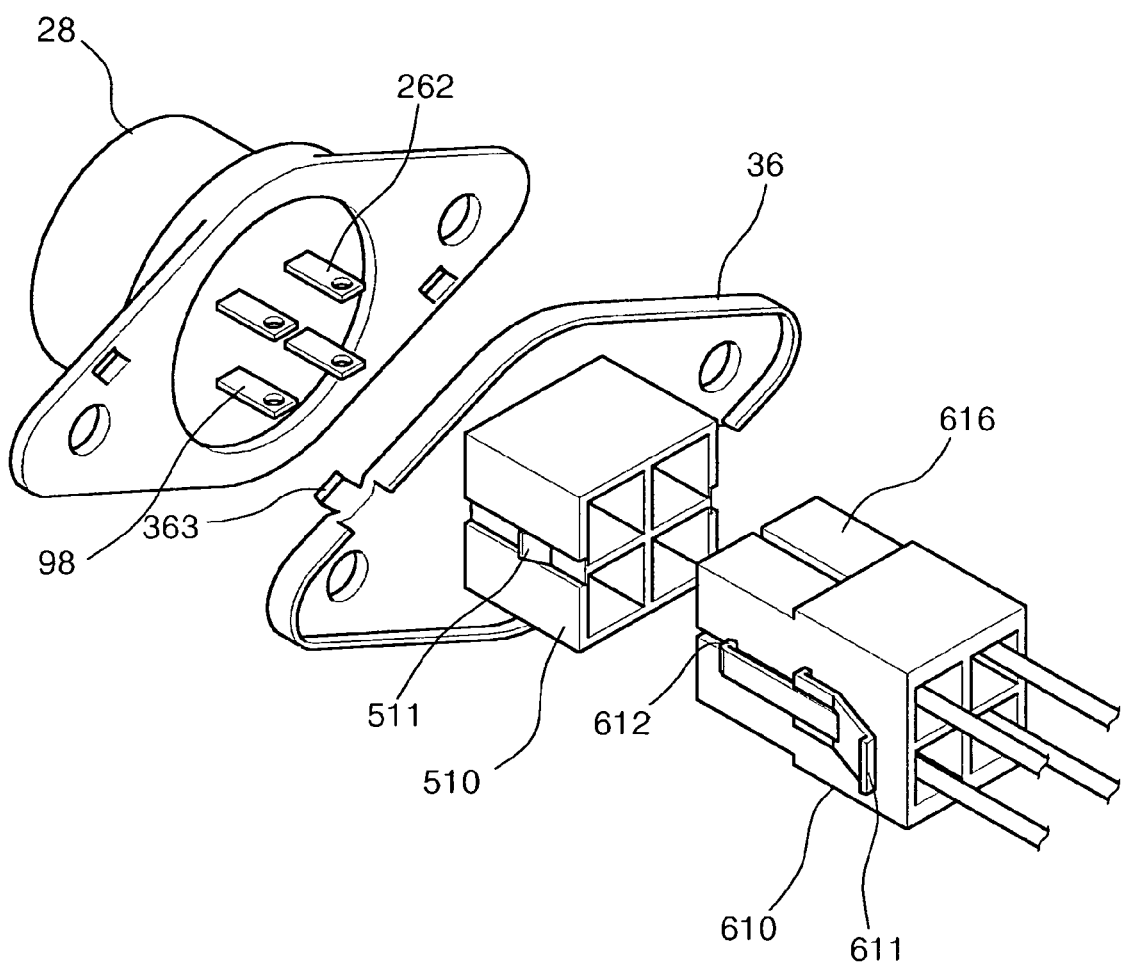
FIG. 28 is an exploded perspective view of the conductivity sensor according to the tenth embodiment of the present invention.

FIG. 27 is a perspective view of the conductivity sensor according to the tenth embodiment of the present invention, and FIG. 28 is an exploded perspective view of the conductivity sensor shown in FIG. 27.

Referring to FIGS. 27 and 28, the conductivity sensor includes the upper protection member 28, the lower protection member 36, the connector 510 formed a lower end portion of the lower protection member 36 in a rectangular shape, and the receptacle 610 fitted into the connector 510. Additionally, the conductivity sensor includes the position manipulating part 616 insertedly fitted into the inner periphery of the connector 510 at a fitting end portion of the receptacle 610, and the fixing protrusion 612 and the latch protrusion 511. The end portion of the receptacle 610 is inserted into the connector 510, such that the position of the receptacle 610 is fixed. The position manipulating part 616 is in contact with an inner or outer surface of the opened portions formed inside the connector 510, thereby firmly supporting the position of the receptacle 610.

This embodiment of the present invention can obtain a stable transmission of electrical signals due to the structures of the connector and the receptacle. Since the washing machine can strongly endure its own vibration due to the above structures of the connector and the receptacle, it is possible to provide a stable sensor structure.

Eleventh Embodiment

An eleventh embodiment of the present invention will be described in detail with reference to FIGS. 29 and 30. The eleventh embodiment of the present invention is mostly identical to the tenth embodiment described above. A difference is a structure that allows the receptacle to be simply and stably fitted into the connector.

Figure 29:
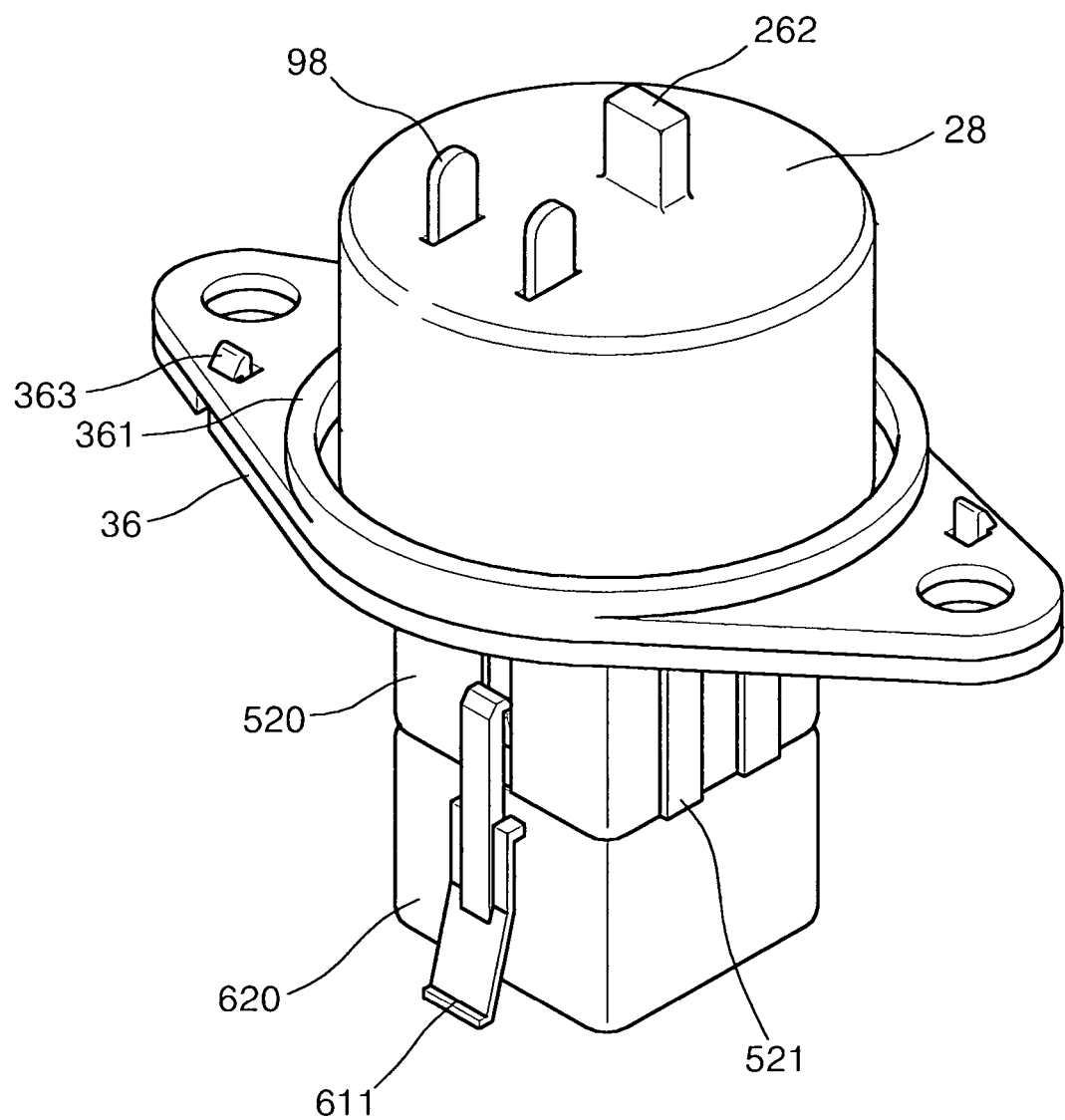
FIG. 29 is a perspective view of a conductivity sensor according to an eleventh embodiment of the present invention.
Figure 30:
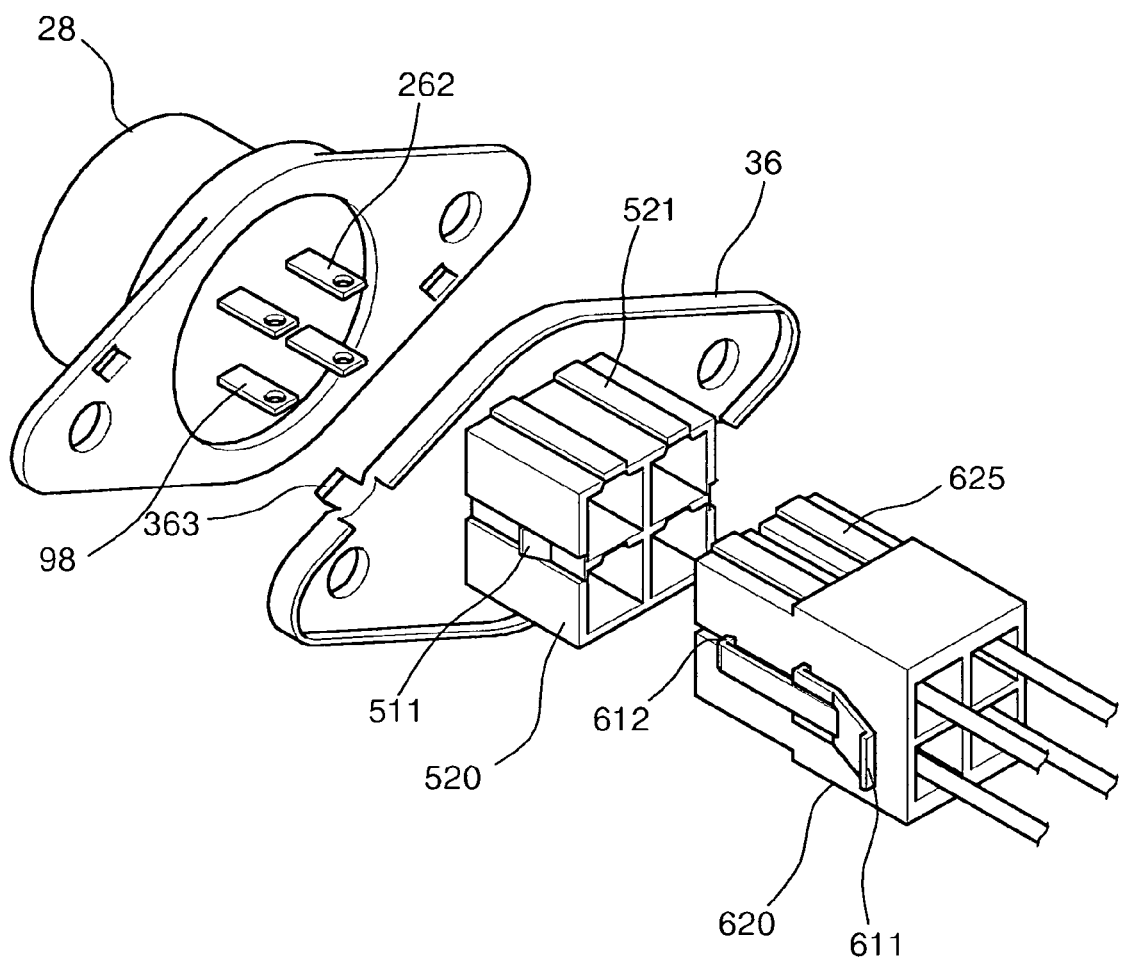
FIG. 30 is an exploded perspective view of the conductivity sensor according to the eleventh embodiment of the present invention.

FIG. 29 is a perspective view of a conductivity sensor according to the eleventh embodiment of the present invention, and FIG. 30 is an exploded perspective view of the conductivity sensor shown in FIG. 29.

Referring to FIGS. 29 and 30, most portions are identical to the tenth embodiment described above. The conductivity sensor further includes a connector guide 521 formed on an outer periphery of the connector 520, a receptacle 620 fitted into the connector 520, and a receptacle guide 625 arranged with the connector guide 521 and formed on an outer periphery of the receptacle 620.

When the receptacle 620 is fitted into the connector 520, the respective guides 521 and 625 are arranged symmetrically, such that the receptacle 620 is fitted accurately. Specifically, the receptacle guide 625 and the connector guide 521 are formed only on one edge, not four edges. Therefore, if the receptacle guide 625 and the connector guide 521 are not arranged correctly, the receptacle 620 cannot be inserted. As a result, when the user inserts the receptacle 620, there is nothing to worry about an incorrect insertion of the electrodes and the temperature sensor, thereby achieving a stable assembly.

Further, due to the forcible insertion of the guides 625 and 521, a coupling force of the receptacle 620 is increased much more.

Hereinafter, a controlling method for operating the washing machine according to the above-described various embodiments will be described.

Figure 31:
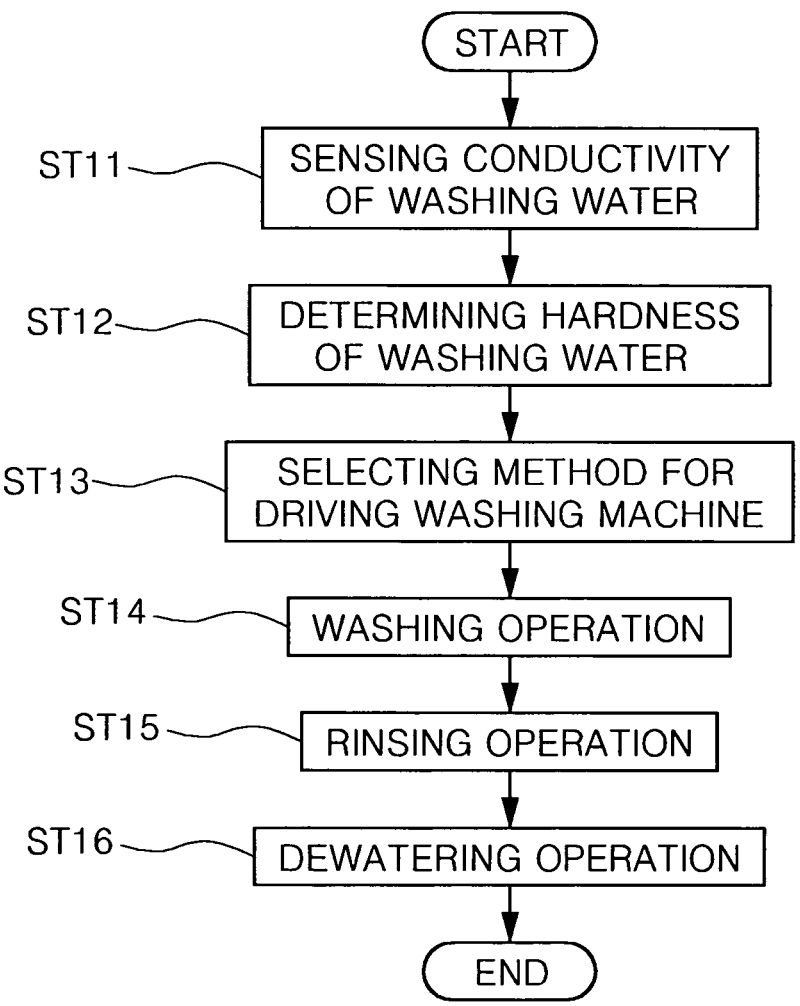
FIG. 31 is a flowchart illustrating a method for controlling a washing machine according to the present invention.

FIG. 31 is a flowchart illustrating a method for controlling the washing machine according to the present invention.

Referring to FIG. 31, if the laundry and the washing water are put in the drum, the conductivity sensor measures the conductivity of the washing water (ST11). Then, the hardness of the washing water is determined using a predetermined equation or a table, which is prepared previously (ST12). The washing water's hardness determined at the step ST12 is used as an information for the entire cycles of the washing machine, which will be performed later. For example, in case the hardness is high, the detergent is not dissolved well. Therefore, the washing cycle is performed with a large amount of detergent and the number of a rinsing operation is decreased. On the contrary, in case the hardness is low, the detergent is dissolved well. Therefore, the washing cycle is performed with a small amount of the detergent and the number of a rinsing operation is increased. Of course, in addition to the hardness of the washing water, the water temperature and the laundry amount can be influenced on the washing cycle.

A driving method of the washing machine is selected according to the hardness determined at the step ST12 (ST13). A washing operation (ST14), a rinsing operation (ST15) and a dewatering operation (ST16) are performed according to the selected driving method. In this manner, the overall washing cycles are completed.

INDUSTRIAL APPLICABILITY

According to the present invention, an optimum washing performance is maintained by properly changing a washing method according to the hardness of the washing water.

Additionally, the reliability in the operation of the washing machine is improved by using the measured conductivity of the washing water as various indexes in the operation of the washing machine.

Further, since the conductivity sensor for measuring the conductivity of the washing machine is installed stably, it is possible to prevent the leakage of the washing water and to operate the washing machine stably.

The invention claimed is:

1. A washing machine comprising:
    a pair of electrodes formed inside an outer tub containing a washing water, for measuring a conductivity of a washing water;
    an upper protection member and a lower protection member through which the electrodes pass, and one of the upper protection member and the lower protection member is inserted into the other of the upper protection member and the lower protection member; and
    a sealing member injected into a space formed between the upper protection member and the lower protection member; and
    a controller for controlling the washing machine according to the measured conductivity of the washing water;
    wherein the end portions of the electrodes are exposed and pass through the sealing member to directly contact with the washing water.

2. The washing machine according to claim 1, wherein the upper protection member and the lower protection member are sealed in a lower portion of the pneumatic chamber sensing a water level.

3. A conductivity sensor of a washing machine, comprising:
    a pair of electrodes formed at one side of an outer tub, for measuring a conductivity of a washing water;
    a protection member for supporting upper and lower portions of the electrodes, the electrodes passing through the protection member, and the protection member forms a closed space therein;
    a sealing member injected into the closed space; and
    a housing in which one side of the protection member is sealed;
    wherein the end portions of the electrodes are exposed and pass through the sealing member to directly contact with the washing water.

4. The conductivity sensor according to claim 3, wherein the protection member includes:
    an upper protection part for supporting an upper portion of the electrodes; and
    a lower protection part for supporting a lower portion of the electrodes.

5. The conductivity sensor according to claim 3, wherein the protection member and the housing are fused with each other.

6. The conductivity sensor according to claim 3, wherein the housing is a chamber housing forming a pneumatic chamber.

7. The conductivity sensor according to claim 3, wherein the sealing member is made of rubber resin or epoxy resin.

8. The conductivity sensor according to claim 3, wherein the sealing member is formed by injecting and solidifying a liquid resin.

9. The conductivity sensor according to claim 3, wherein the housing is a chamber housing of a pneumatic chamber for measuring a water level.

10. The conductivity sensor according to claim 3, further comprising a shield member for preventing an erroneous operation due to foreign substance between the electrodes.

11. The conductivity sensor according to claim 3, further comprising a shield member formed between the electrodes by convexly forming the sealing member.

12. The conductivity sensor according to claim 3, further comprising a shield member formed between the electrodes to prevent an erroneous operation due to foreign substance, a thickness of the shield member being reduced in an upward direction.

* * * * *